US012653608B2

(12) United States Patent
Schultheis et al.

(10) Patent No.: US 12,653,608 B2
(45) Date of Patent: Jun. 16, 2026

(54) OPTOELECTRICAL CONNECTOR FOR INTRAVASCULAR LITHOTRIPSY DEVICE

(71) Applicant: Boston Scientific Scimed, Inc., Maple Grove, MN (US)

(72) Inventors: Eric Schultheis, San Clemente, CA (US); Alvin Salinas, San Marcos, CA (US); Peter Dahl, Carlsbad, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 319 days.

(21) Appl. No.: 18/365,101

(22) Filed: Aug. 3, 2023

(65) Prior Publication Data

US 2024/0041520 A1     Feb. 8, 2024

Related U.S. Application Data

(60) Provisional application No. 63/395,853, filed on Aug. 7, 2022.

(51) Int. Cl.
*A61B 18/14*     (2006.01)
*G02B 6/42*     (2006.01)
*A61B 18/00*     (2006.01)

(52) U.S. Cl.
CPC ........ *A61B 18/1492* (2013.01); *G02B 6/4225* (2013.01); *G02B 6/4261* (2013.01);
(Continued)

(58) Field of Classification Search
CPC ..... A61B 18/1492; A61B 18/22; A61B 18/24; A61B 18/26; A61B 2018/00172;
(Continued)

(56) References Cited

U.S. PATENT DOCUMENTS

| | | | |
|---|---|---|---|
| 4,649,924 A | 3/1987 | Taccardi | |
| 4,699,147 A | 10/1987 | Chilson et al. | |

(Continued)

FOREIGN PATENT DOCUMENTS

| | | |
|---|---|---|
| AU | 2017205323 | 7/2017 |
| AU | 2022227829 | 9/2022 |

(Continued)

OTHER PUBLICATIONS

Definition of ablation—NCI Dictionary of Cancer Terms—NCI, National Cancer Institute, p. 1 (Year:2025).

(Continued)

*Primary Examiner* — Tigist S Demie
(74) *Attorney, Agent, or Firm* — Seager, Tufte & Wickhem, LLP

(57)     ABSTRACT

A catheter system (100) for treating a treatment site (106) includes a catheter (102), a system console (123) that includes a console connection aperture (148), an energy source (124), one or more energy guides (122A) that receive energy from the energy source (124), and an optoelectrical connector (151) that is coupled to the catheter (102). The optoelectrical connector (151) includes a guide coupling housing (250) that retains at least a portion of each of the energy guides (122A). The guide coupling housing (250) is configured to be selectively mechanically connected to the system console (123) via the console connection aperture (148) so that the energy guides (122A) are adjustably aligned relative to the energy from the energy source (124). The optoelectrical connector (151) also includes at least a portion of an electrical connector assembly that is positioned adjacent to the guide coupling housing (250) and that transmits at least one of power and data between the system console (123) and the catheter (102) when the guide cou- (Continued)

pling housing (250) is retained within the console connection aperture (148).

20 Claims, 5 Drawing Sheets

(52) U.S. Cl.
  CPC ........... *G02B 6/428* (2013.01); *G02B 6/4296* (2013.01); *A61B 2018/0022* (2013.01)

(58) Field of Classification Search
  CPC .. A61B 2018/00178; A61B 2018/0022; A61B 2018/00345; A61B 2018/2211; G02B 6/001; G02B 6/3817; G02B 6/3878; G02B 6/4225; G02B 6/4261; G02B 6/428; G02B 6/4293; G02B 6/4296
  See application file for complete search history.

(56) References Cited

U.S. PATENT DOCUMENTS

| | | |
|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Suglyama |
| 4,960,108 A | 10/1990 | Reichel et al. |
| 4,994,059 A | 2/1991 | Kosa et al. |
| 4,998,930 A | 3/1991 | Lundahl |
| 5,019,075 A | 5/1991 | Spears et al. |
| 5,034,010 A | 7/1991 | Kittrell et al. |
| 5,041,121 A | 8/1991 | Wondrazek et al. |
| 5,057,106 A | 10/1991 | Kasevich et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A | 1/1993 | Makita et al. |
| 5,188,632 A | 2/1993 | Goldenberg |
| 5,200,838 A | 4/1993 | Nudelman |
| 5,269,777 A | 12/1993 | Doiron |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,363,458 A | 11/1994 | Pan |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,417,689 A | 5/1995 | Fine |
| 5,422,926 A | 6/1995 | Smith |
| 5,431,647 A | 7/1995 | Purcell |
| 5,454,809 A | 10/1995 | Janssen |
| 5,456,680 A | 10/1995 | Taylor |
| 5,474,537 A | 12/1995 | Solar |
| 5,496,311 A | 3/1996 | Abele et al. |
| 5,509,917 A | 4/1996 | Cecchetti |
| 5,519,798 A | 5/1996 | Shahid |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,637,877 A | 6/1997 | Sinofsky |
| 5,661,829 A | 8/1997 | Zheng |
| 5,697,377 A | 12/1997 | Wittkamph |
| 5,718,241 A | 2/1998 | Ben-Haim et al. |
| 5,729,583 A | 3/1998 | Tang |
| 5,764,843 A | 6/1998 | Macken et al. |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,007,514 A | 12/1999 | Nita |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,423,055 B1 | 7/2002 | Farr |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 2/2003 | Rabiner et al. |
| 6,538,739 B1 | 3/2003 | Visuri et al. |
| 6,544,218 B1 | 4/2003 | Choi |
| 6,548,010 B1 | 4/2003 | Stivland et al. |
| 6,560,387 B1 | 5/2003 | Hehlen et al. |
| 6,607,502 B1 | 8/2003 | Maguire et al. |
| 6,631,220 B1 | 10/2003 | Liang et al. |
| 6,652,547 B2 | 11/2003 | Rabiner et al. |
| 6,666,834 B2 | 12/2003 | Restle et al. |
| 6,702,781 B1 | 3/2004 | Reifart et al. |
| 6,773,447 B2 | 8/2004 | Laguna |
| 6,824,554 B1 | 11/2004 | Jang |
| 6,849,994 B1 | 2/2005 | White et al. |
| 6,890,317 B2 | 5/2005 | Gerdts et al. |
| 6,947,785 B1 | 9/2005 | Beatty et al. |
| 6,966,890 B2 | 11/2005 | Coyle et al. |
| 6,978,168 B2 | 12/2005 | Beatty et al. |
| 6,990,370 B1 | 1/2006 | Beatty et al. |
| 7,273,470 B2 | 9/2007 | Wantink |
| 7,309,324 B2 | 12/2007 | Hayes et al. |
| 7,367,967 B2 | 5/2008 | Eidenschink |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,641,646 B2 | 1/2010 | Kennedy, II |
| 7,691,079 B2 | 4/2010 | Gobel |
| 7,713,260 B2 | 5/2010 | Lessard |
| 7,758,572 B2 | 7/2010 | Weber et al. |
| 7,762,984 B2 | 7/2010 | Kumoyama et al. |
| 7,810,395 B2 | 10/2010 | Zhou |
| 7,850,685 B2 | 12/2010 | Kunis et al. |
| 7,867,178 B2 | 1/2011 | Simnacher |
| 7,909,797 B2 | 3/2011 | Kennedy, II et al. |
| 7,942,850 B2 | 5/2011 | Levit et al. |
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter |
| 8,043,256 B2 | 10/2011 | Hansen |
| 8,066,732 B2 | 11/2011 | Paul et al. |
| 8,088,121 B2 | 1/2012 | Nishide |
| 8,157,760 B2 | 4/2012 | Criado et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,197,505 B2 | 6/2012 | Hirszowicz et al. |
| 8,246,643 B2 | 8/2012 | Nita |
| 8,267,886 B2 | 9/2012 | Ewing |
| 8,292,913 B2 | 10/2012 | Warnack |
| 8,328,820 B2 | 12/2012 | Diamant |
| 8,364,235 B2 | 1/2013 | Kordis et al. |
| 8,372,034 B2 | 2/2013 | Levit |
| 8,382,738 B2 | 2/2013 | Simpson et al. |
| 8,414,527 B2 | 4/2013 | Mallaby |
| 8,419,613 B2 | 4/2013 | Saadat |

(56)     References Cited

U.S. PATENT DOCUMENTS

| | | | |
|---|---|---|---|
| 8,439,890 | B2 | 5/2013 | Beyar |
| 8,556,813 | B2 | 10/2013 | Cashman et al. |
| 8,556,851 | B2 | 10/2013 | Hirszowicz |
| 8,574,247 | B2 | 11/2013 | Adams et al. |
| 8,657,814 | B2 | 2/2014 | Werneth |
| 8,709,075 | B2 | 4/2014 | Adams et al. |
| 8,728,091 | B2 | 5/2014 | Hakala et al. |
| 8,734,424 | B2 | 5/2014 | Watanabe |
| 8,747,416 | B2 | 6/2014 | Hakala et al. |
| 8,784,362 | B2 | 7/2014 | Boutilette |
| 8,834,510 | B2 | 9/2014 | Wilson et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 8,986,339 | B2 | 3/2015 | Warnack |
| 8,992,519 | B2 | 3/2015 | Kim et al. |
| 8,992,817 | B2 | 3/2015 | Stamberg |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,011,511 | B2 | 4/2015 | Gregorich |
| 9,044,575 | B2 | 6/2015 | Beasley et al. |
| 9,044,618 | B2 | 6/2015 | Hawkins et al. |
| 9,044,619 | B2 | 6/2015 | Hawkins et al. |
| 9,056,185 | B2 | 6/2015 | Fischell et al. |
| 9,072,534 | B2 | 7/2015 | Adams et al. |
| 9,089,669 | B2 | 7/2015 | Haslinger et al. |
| 9,131,949 | B2 | 9/2015 | Coleman et al. |
| 9,138,249 | B2 | 9/2015 | Adams et al. |
| 9,138,260 | B2 | 9/2015 | Miller et al. |
| 9,180,280 | B2 | 11/2015 | Hawkins et al. |
| 9,220,521 | B2 | 12/2015 | Hawkins et al. |
| 9,237,984 | B2 | 1/2016 | Hawkins et al. |
| 9,254,169 | B2 | 2/2016 | Long et al. |
| 9,282,984 | B2 | 3/2016 | Nita |
| 9,283,359 | B2 | 3/2016 | Pepper |
| 9,289,132 | B2 | 3/2016 | Ghaffari et al. |
| 9,289,224 | B2 | 3/2016 | Adams et al. |
| 9,289,319 | B2 | 3/2016 | Pacetti et al. |
| 9,320,530 | B2 | 4/2016 | Grace |
| 9,333,000 | B2 | 5/2016 | Hakala et al. |
| 9,339,632 | B2 | 5/2016 | Eidenschink et al. |
| 9,364,645 | B2 | 6/2016 | Erikawa |
| 9,375,223 | B2 | 6/2016 | Wallace |
| 9,421,025 | B2 | 8/2016 | Hawkins et al. |
| 9,433,428 | B2 | 9/2016 | Hakala et al. |
| 9,433,745 | B2 | 9/2016 | Cully |
| 9,504,809 | B2 | 11/2016 | Bo |
| 9,510,887 | B2 | 12/2016 | Burnett |
| 9,522,012 | B2 | 12/2016 | Adams |
| 9,554,815 | B2 | 1/2017 | Adams et al. |
| 9,555,267 | B2 | 1/2017 | Ein-gal |
| 9,566,209 | B2 | 2/2017 | Katragadda et al. |
| 9,579,114 | B2 | 2/2017 | Mantell et al. |
| 9,579,492 | B2 | 2/2017 | Simpson |
| 9,585,684 | B2 | 3/2017 | Nita et al. |
| 9,592,328 | B2 | 3/2017 | Jeevanandam |
| 9,603,506 | B2 | 3/2017 | Goldfarb et al. |
| 9,629,567 | B2 | 4/2017 | Porath et al. |
| 9,642,673 | B2 | 5/2017 | Adams |
| 9,662,069 | B2 | 5/2017 | De Graff et al. |
| 9,687,166 | B2 | 6/2017 | Subramaniam |
| 9,700,655 | B2 | 7/2017 | Laudenslager et al. |
| 9,730,715 | B2 | 8/2017 | Adams |
| 9,737,361 | B2 | 8/2017 | Magana |
| 9,764,142 | B2 | 9/2017 | Imran |
| 9,782,570 | B2 | 10/2017 | Hirszowicz |
| 9,814,476 | B2 | 11/2017 | Adams et al. |
| 9,833,348 | B2 | 12/2017 | Jordan et al. |
| 9,839,764 | B2 | 12/2017 | Chouinard |
| 9,861,377 | B2 | 1/2018 | Mantell et al. |
| 9,867,629 | B2 | 1/2018 | Hawkins et al. |
| 9,878,135 | B2 | 1/2018 | Holzapfel et al. |
| 9,894,756 | B2 | 2/2018 | Weinkam et al. |
| 9,901,704 | B2 | 2/2018 | Appling |
| 9,955,946 | B2 | 5/2018 | Miller et al. |
| 9,974,963 | B2 | 5/2018 | Imran |
| 9,974,970 | B2 | 5/2018 | Nuta et al. |
| 9,993,292 | B2 | 6/2018 | Adams et al. |
| 10,039,561 | B2 | 8/2018 | Adams et al. |
| 10,076,384 | B2 | 9/2018 | Kasprzyk |
| 10,086,175 | B2 | 10/2018 | Torres et al. |
| 10,124,153 | B2 | 11/2018 | Feig |
| 10,136,829 | B2 | 11/2018 | Deno et al. |
| 10,149,690 | B2 | 12/2018 | Hawkins et al. |
| 10,159,505 | B2 | 12/2018 | Hakala et al. |
| 10,194,994 | B2 | 2/2019 | Deno et al. |
| 10,201,387 | B2 | 2/2019 | Grace et al. |
| 10,206,698 | B2 | 2/2019 | Hakala et al. |
| 10,226,265 | B2 | 3/2019 | Ku et al. |
| 10,245,410 | B2 | 4/2019 | Aggerholm |
| 10,327,846 | B1 | 6/2019 | Stark et al. |
| 10,328,290 | B2 | 6/2019 | Zhou et al. |
| 10,357,264 | B2 | 7/2019 | Kat-Kuoy |
| 10,405,923 | B2 | 9/2019 | Yu et al. |
| 10,406,031 | B2 | 9/2019 | Thyzel |
| 10,406,318 | B2 | 9/2019 | Williams |
| 10,420,569 | B2 | 9/2019 | Adams |
| 10,439,791 | B2 | 10/2019 | Kalhan |
| 10,441,300 | B2 | 10/2019 | Hawkins |
| 10,449,339 | B2 | 10/2019 | Wilson et al. |
| 10,463,430 | B2 | 11/2019 | Dick |
| 10,478,202 | B2 | 11/2019 | Adams et al. |
| 10,517,620 | B2 | 12/2019 | Adams |
| 10,517,621 | B1 | 12/2019 | Hakala et al. |
| 10,537,287 | B2 | 1/2020 | Braido et al. |
| 10,555,744 | B2 | 2/2020 | Nguyen et al. |
| 10,561,428 | B2 | 2/2020 | Eggert et al. |
| 10,583,277 | B2 | 3/2020 | Rundquist |
| 10,589,073 | B2 | 3/2020 | Mallaby |
| 10,617,850 | B2 | 4/2020 | Tal |
| 10,646,240 | B2 | 5/2020 | Betelia et al. |
| 10,668,245 | B2 | 6/2020 | Kanae |
| 10,682,178 | B2 | 6/2020 | Adams et al. |
| 10,695,531 | B2 | 6/2020 | Suzuki |
| 10,702,293 | B2 | 7/2020 | Adams et al. |
| 10,709,462 | B2 | 7/2020 | Nguyen et al. |
| 10,709,872 | B2 | 7/2020 | Alvarez et al. |
| 10,758,255 | B2 | 9/2020 | Adams |
| 10,797,684 | B1 | 10/2020 | Benz et al. |
| 10,799,688 | B2 | 10/2020 | Calhoun |
| 10,842,567 | B2 | 11/2020 | Grace et al. |
| 10,850,075 | B2 | 12/2020 | Tarunaga |
| 10,857,329 | B2 | 12/2020 | Davies |
| 10,933,225 | B2 | 3/2021 | Campbell |
| 10,952,740 | B2 | 3/2021 | Dasnurkar et al. |
| 10,952,790 | B2 | 3/2021 | Haverkost et al. |
| 10,959,743 | B2 | 3/2021 | Adams et al. |
| 10,966,737 | B2 | 4/2021 | Nguyen |
| 10,967,156 | B2 | 4/2021 | Gulachenski |
| 10,973,538 | B2 | 4/2021 | Hakala et al. |
| 10,974,028 | B2 | 4/2021 | Buller et al. |
| 10,980,987 | B2 | 4/2021 | Tarunaga |
| 11,000,299 | B2 | 5/2021 | Hawkins et al. |
| 11,020,135 | B1 | 6/2021 | Hawkins |
| 11,026,707 | B2 | 6/2021 | Ku et al. |
| 11,040,176 | B2 | 6/2021 | Blanchard et al. |
| 11,058,492 | B2 | 7/2021 | Grace et al. |
| 11,076,874 | B2 | 8/2021 | Hakala et al. |
| 11,116,939 | B2 | 9/2021 | Jamous et al. |
| 11,141,131 | B2 | 10/2021 | Stigall |
| 11,179,169 | B2 | 11/2021 | Brouillete et al. |
| 11,207,493 | B2 | 12/2021 | Suzuki et al. |
| 11,213,661 | B2 | 1/2022 | Spindler |
| 11,229,772 | B2 | 1/2022 | Nita |
| 11,229,776 | B2 | 1/2022 | Kugler et al. |
| 11,246,659 | B2 | 2/2022 | Grace et al. |
| 11,253,681 | B2 | 2/2022 | Williams |
| 11,266,817 | B2 | 3/2022 | Cope et al. |
| 11,389,171 | B2 | 7/2022 | Goldsmith |
| 11,389,628 | B2 | 7/2022 | Spencer |
| 11,395,669 | B2 | 7/2022 | O'Malley et al. |
| 11,399,862 | B2 | 8/2022 | Massimini et al. |
| 11,406,452 | B2 | 8/2022 | Efremkin |

(56) References Cited

U.S. PATENT DOCUMENTS

| | | |
|---|---|---|
| 11,406,799 B2 | 8/2022 | McEvaddy et al. |
| 11,484,327 B2 | 11/2022 | Anderson et al. |
| 11,540,848 B2 | 1/2023 | Cai et al. |
| 11,564,729 B2 | 1/2023 | Walzman |
| 11,602,363 B2 | 3/2023 | Nguyen |
| 11,633,200 B2 | 4/2023 | Anderson et al. |
| 11,672,585 B2 | 6/2023 | Schultheis |
| 11,672,599 B2 | 6/2023 | Schultheis et al. |
| 11,707,323 B2 | 7/2023 | Schultheis et al. |
| 11,771,449 B2 | 10/2023 | Adams et al. |
| 11,779,363 B2 | 10/2023 | Vo |
| 11,826,530 B2 | 11/2023 | Suzuki |
| 11,839,391 B2 | 12/2023 | Schultheis et al. |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 11,950,793 B2 | 4/2024 | Nguyen |
| 12,011,185 B2 | 6/2024 | Vo |
| 12,023,098 B2 | 7/2024 | Nguyen |
| 12,035,932 B1 | 7/2024 | Nunes |
| 12,076,077 B2 | 9/2024 | Mori |
| 12,144,516 B2 | 11/2024 | Betelia |
| 12,178,458 B1 | 12/2024 | Betelia et al. |
| 12,193,691 B2 | 1/2025 | Adams |
| 2001/0016761 A1 | 8/2001 | Rudie |
| 2001/0018569 A1 | 8/2001 | Erbel |
| 2001/0020164 A1 | 9/2001 | Papademetriou |
| 2001/0049464 A1 | 12/2001 | Ganz |
| 2001/0051784 A1 | 12/2001 | Brisken |
| 2002/0045811 A1 | 4/2002 | Kittrell et al. |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0142703 A1 | 6/2006 | Carter |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142779 A1 | 6/2007 | Duane |
| 2007/0142819 A1 | 6/2007 | El-Nounou et al. |
| 2007/0142821 A1 | 6/2007 | Hennessy et al. |
| 2007/0142856 A1 | 6/2007 | Jang |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036238 A1 | 2/2010 | Neidert |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0286791 A1 | 11/2010 | Goldsmith |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |

(56) References Cited

U.S. PATENT DOCUMENTS

| | | |
|---|---|---|
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0323211 A1 | 12/2012 | Ogle |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0060234 A1 | 3/2013 | Besser |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 2/2014 | Diodone et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0128848 A1 | 5/2014 | Appling et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336626 A1 | 11/2014 | Jiang |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0071591 A1 | 3/2015 | Chen |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0342681 A1 | 12/2015 | Lee |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1* | 1/2016 | Govari ................ G02B 6/3826 385/71 |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0234534 A1 | 8/2016 | Kitahara et al. |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0324564 A1 | 11/2016 | Gerlach et al. |
| 2016/0331389 A1 | 11/2016 | Hakala et al. |
| 2016/0339204 A1 | 11/2016 | Williams |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 5/2018 | Thumpudi et al. |
| 2018/0169392 A1 | 6/2018 | Franklin |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |

(56) References Cited

U.S. PATENT DOCUMENTS

| | | |
|---|---|---|
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0150961 A1 | 5/2019 | Tozzi |
| 2019/0159792 A1 | 5/2019 | Panian |
| 2019/0167349 A1 | 6/2019 | Shamay |
| 2019/0175111 A1 | 6/2019 | Genereux et al. |
| 2019/0175300 A1 | 6/2019 | Hom |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0285803 A1 | 9/2019 | Van Zuylen |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2019/0388654 A1 | 12/2019 | Chou |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0129742 A1* | 4/2020 | Cope ............... A61B 17/22022 |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0345380 A1 | 11/2020 | Boyle et al. |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0001138 A1 | 1/2022 | Howell |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0040454 A1 | 2/2022 | Hamm |
| 2022/0054194 A1 | 2/2022 | Bacher et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0249166 A1 | 8/2022 | Cook et al. |
| 2022/0273324 A1 | 9/2022 | Schultheis |
| 2022/0287732 A1 | 9/2022 | Anderson et al. |
| 2022/0313293 A1 | 10/2022 | Singh |
| 2022/0313359 A1 | 10/2022 | Schultheis et al. |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0064371 A1 | 3/2023 | Cook et al. |
| 2023/0137107 A1 | 5/2023 | Cook et al. |
| 2023/0157754 A1 | 5/2023 | Bacher et al. |
| 2023/0200906 A1 | 6/2023 | Cook et al. |
| 2023/0233256 A1 | 7/2023 | Cook et al. |
| 2023/0240748 A1 | 8/2023 | Cook et al. |
| 2023/0248376 A1 | 8/2023 | Anderson et al. |
| 2023/0255635 A1 | 8/2023 | Schultheis et al. |
| 2023/0255688 A1 | 8/2023 | Schultheis et al. |
| 2023/0255689 A1 | 8/2023 | Schultheis et al. |
| 2023/0310054 A1 | 10/2023 | Schultheis |
| 2023/0310067 A1 | 10/2023 | Schultheis et al. |
| 2023/0310073 A1 | 10/2023 | Adams et al. |
| 2023/0320576 A1 | 10/2023 | Feldman |
| 2023/0338088 A1 | 10/2023 | Massimini et al. |
| 2023/0338089 A1 | 10/2023 | Schultheis |
| 2023/0414234 A1 | 12/2023 | Anderson et al. |
| 2024/0001076 A1 | 1/2024 | Gelsinger |
| 2024/0016508 A1 | 1/2024 | Kocur |
| 2024/0016544 A1 | 1/2024 | Schultheis et al. |
| 2024/0016545 A1 | 1/2024 | Schultheis et al. |
| 2024/0023813 A1 | 1/2024 | Milner |
| 2024/0032995 A1 | 2/2024 | Schultheis et al. |
| 2024/0033002 A1 | 2/2024 | Cook |
| 2024/0041520 A1 | 2/2024 | Schultheis et al. |
| 2024/0050170 A1 | 2/2024 | Fournier |
| 2024/0050696 A1 | 2/2024 | Japuntich |
| 2024/0058060 A1 | 2/2024 | Cook |
| 2024/0065711 A1 | 2/2024 | Hendrickson |
| 2024/0065712 A1 | 2/2024 | Schultheis |
| 2024/0099773 A1 | 3/2024 | Schabert |

(56) References Cited

U.S. PATENT DOCUMENTS

| | | |
|---|---|---|
| 2024/0122648 A1 | 4/2024 | Cook |
| 2024/0165658 A1 | 5/2024 | Fu |
| 2024/0173044 A1 | 5/2024 | Chen et al. |
| 2024/0173526 A1 | 5/2024 | Kofidis |
| 2024/0189543 A1 | 6/2024 | Salinas |
| 2024/0216062 A1 | 7/2024 | Cook |
| 2024/0260981 A1 | 8/2024 | Betelia |
| 2024/0260982 A1 | 8/2024 | Peterson |
| 2024/0277410 A1 | 8/2024 | Cook |
| 2024/0277974 A1 | 8/2024 | Oehler |
| 2024/0277980 A1 | 8/2024 | O'Neill |
| 2024/0285296 A1 | 8/2024 | Vo |
| 2024/0285922 A1 | 8/2024 | Chu |
| 2024/0299051 A1 | 9/2024 | Sidhu et al. |
| 2024/0307119 A1 | 9/2024 | Nguyen |
| 2024/0325045 A1 | 10/2024 | Otake |
| 2024/0382258 A1 | 11/2024 | Schultheis |
| 2025/0025237 A1 | 1/2025 | Cook |
| 2025/0040947 A1 | 2/2025 | Schultheis |

FOREIGN PATENT DOCUMENTS

| | | |
|---|---|---|
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| CN | 117752412 | 3/2024 |
| CN | 118055734 | 5/2024 |
| DE | 3038445 A1 | 5/1982 |
| DE | 3836337 A1 | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 0547146 | 7/1995 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2470248 | 7/2012 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 2961463 | 5/2019 |
| EP | 3240603 | 5/2019 |
| EP | 3197381 | 3/2020 |
| EP | 3643260 A1 | 4/2020 |
| EP | 3240494 | 3/2021 |
| EP | 3522812 | 12/2021 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 4146322 | 4/2024 |
| EP | 3182931 | 6/2024 |
| EP | 3950036 | 8/2024 |
| EP | 4034005 | 12/2024 |
| GB | 1082397 | 9/1967 |
| JP | S62275446 A | 11/1987 |
| JP | H05264763 | 10/1993 |
| JP | 1996089511 | 4/1996 |
| JP | H09117407 | 5/1997 |
| JP | 2001520070 | 10/2001 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2012505050 | 3/2012 |
| JP | 2014123147 | 7/2014 |
| JP | A2014516614 | 7/2014 |
| JP | A2015522344 | 8/2015 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 | 12/2009 |
| WO | 2010042653 A1 | 4/2010 |
| WO | WO2011094379 | 8/2011 |
| WO | 20110126580 A2 | 10/2011 |
| WO | WO2011126580 A3 | 10/2011 |

(56)　　　References Cited

FOREIGN PATENT DOCUMENTS

| | | |
|---|---|---|
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256693 | 12/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |
| WO | WO2024079108 | 4/2024 |
| WO | WO2024107418 | 5/2024 |

OTHER PUBLICATIONS

Daemen, J., Tovar Forero, M.N, "The Coronary Intravascular Lithotripsy System", ICR Journal, 2019; 14(3); 174-181.

Butt, N., Khalid, N., Shlofmitz, E., "Intravascular Lithotripsy"; NCBI Bookshelf. A service of the National Library of Medicine, National Institutes of Health; StatPearls Publishing, 2023.

"Custom Medical Skived Tubing", Duke Extrusion, 2025. https://www.dukeextrusion.com/tubing-options/skived-tubing.

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

Bian, D. C., et al. "Study on Breakdown Delay Characteristics Based on High-voltage Pulse Discharge in Water with Hydrostatic Pressure", Journal of Power Technologies 97(2), 2017, pp. 89-102.

Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.

Brodmann, Marianne et al. "Safety and Performance of Lithoplasty for Treatment of Calcified Peripheral Artery Lesions", JACC, 2017, vol. 70, No. 7.

Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.

"Bubble Dynamics and Shock Waves", Springer, 2013, Springer-Verlag, Berlin Heildelberg.

Hardy, Luke A., et al. "Cavitation Bubble Dynamics During Thulium Fiber Laser Lithotripsy", SPIE, Feb. 29, 2016, vol. 9689, San Francisco, California, USA.

Claverie, A., et al. "Experimental characterization of plasma formation and shockwave propagation induced by high power pulsed underwater electrical discharge", Review of Scientific Instruments, 2014, American Institute of Physics.

Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.

Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.

(56) References Cited

OTHER PUBLICATIONS

Cook, Jason R., et al. "Tissue mimicking phantoms for photoacoustic and ultrasonic imaging", Biomedical Optics Express, 2011, vol. 2, No. 11, Optical Society of America.

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, p. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

(56) References Cited

OTHER PUBLICATIONS

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Varghese, B., et al. "Influence of absorption induced thermal initiation pathway on irradiance threshold for laser induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European Application No. 18185152, mailed Dec. 13, 20188.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, mailed Jan. 16, 2019.

European Search Report, for European Patent Application No. 18185152.8, mailed Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Artificial Stones For Research On The Mechinisms Of Stone Breakage In Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland. 2015.

Medlight, "Cylindircal light diffuser Model RD", Medlight S.A., Switzerland. 2015.

Mayo, Michael E., "Interaction of Laser Radiation with Urinary Calculi", Cranfield University Defense and Security, PhD Thesis, 2009, Cranfield University.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

(56)  References Cited

OTHER PUBLICATIONS

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing. Oct. 2015.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

International Preliminary Report on Patentability dated Sep. 15, 2020 in PCT Application Serial No. PCT/US2019/022009.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

Schafter+Kirchhoff, Laser Beam Couplers series 60SMS for coupling into single-mode and polarization-maintaining fiber cables, Schafter+Kirchhoff, pp. 1-5, Germany. Dec. 2, 2021.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

Partial Search Report and Provisional Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery Of Atrial Endocardial Potential Maps From Non-contact Electrode Data." Auckland Bioengineering Institute. (ID 1421). May 2019.

Jiang et al., "Multielectrode Catheter For Substrate Mapping For Scar-related VT Ablation: A Comparison Between Grid Versus

(56) References Cited

OTHER PUBLICATIONS

Linear Configurations." UChicago Medicine, Center for Arrhythmia Care, Chicago IL (ID 1368). Poster for conference in San Francisco, May 8-11, 2019.

Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019.

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Aug. 20, 2021 in PCT Application Serial No. PCT/US2021/031130.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

International Search Report and Written Opinion dated Aug. 25, 2022 in PCT Application Serial No. PCTUS/2022/028035.

International Search Report and Written Opinion dated Sep. 15, 2022 in PCT Application Serial No. PCTUS/2022/032045.

International Search Report and Written Opinion dated Nov. 8, 2022 in PCT Application Serial No. PCTUS/2022/039678.

International Search Report and Written Opinion, PCT Application Serial No. PCT/US2022/047751 issued Feb. 10, 2023, by the European Patent Office.

International Search Report and Written Opinion, PCT Application Serial No. PCT/US2022/047691 issued Feb. 13, 2023, by the European Patent Office.

Accucoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023.

International Search Report and Written Opinion issued by the European Patent Office, for Serial No. PCT/US2023/011497, dated Apr. 28, 2023.

International Search Report and Written Opinion issued by the European Patent Office, for Serial No. PCT/US2023/012599, dated May 19, 2023.

PathFinder Digital, "Free Space Optics vs. Fiber Optics", 2023.

International Search Report and Written Opinion, issued in Application Serial No. PCT/US2023/016152, dated Jul. 12, 2023.

Shen, Yajie et al. "High-peak-power and narrow-linewidth Q-switched Ho: YAG laser in-band pumped at 1931 nm." Applied Physics Express 13.5 (2020): 052006. (Year 2020).

* cited by examiner

OPTOELECTRICAL CONNECTOR FOR INTRAVASCULAR LITHOTRIPSY DEVICE

RELATED APPLICATION

This Application is related to and claims priority on U.S. Provisional Patent Application Ser. No. 63/395,853 filed on Aug. 7, 2022, and entitled "OPTOELECTRICAL CONNECTOR FOR INTRAVASCULAR LITHOTRIPSY DEVICE". To the extent permissible, the contents of U.S. Application Ser. No. 63/395,853 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Intravascular lithotripsy is one method that has been recently used with some success for breaking up vascular lesions within vessels in the body. Intravascular lithotripsy utilizes a combination of pressure waves and bubble dynamics that are generated intravascularly in a fluid-filled balloon catheter. In particular, during an intravascular lithotripsy treatment, a high energy source is used to generate plasma and ultimately pressure waves as well as a rapid bubble expansion within a fluid-filled balloon to crack calcification at a treatment site within the vasculature that includes one or more vascular lesions. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

There is an ongoing desire to enhance vessel patency and optimization of therapy delivery parameters within an intravascular lithotripsy catheter system in a manner that is relatively easy to control and is consistently manufacturable.

SUMMARY

The present invention is directed toward a catheter system for treating a treatment site within or adjacent to a blood vessel within a body of a patient. In various embodiments, the catheter system includes a catheter, a system console, an energy source, one or more energy guides, and an optoelectrical connector. The system console includes a console connection aperture. The energy source is configured to generate energy. The one or more energy guides are configured to receive the energy from the energy source. The optoelectrical connector is coupled to the catheter. The optoelectrical connector includes a guide coupling housing that retains at least a portion of each of the one or more energy guides. The guide coupling housing is configured to be selectively mechanically connected to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source. The optoelectrical connector also includes at least a portion of an electrical connector assembly that is positioned adjacent to the guide coupling housing and that transmits at least one of power and data between the system console and the catheter when the guide coupling housing is retained within the console connection aperture.

In many embodiments, the electrical connection assembly includes a first electrical connector that is positioned within the system console, and a second electrical connector that is positioned adjacent to the guide coupling housing. The second electrical connector is configured to interface with the first electrical connector when the guide coupling housing is retained within the console connection aperture.

In some embodiments, the second electrical connector includes a connector base and a plurality of electrical connection pads that are coupled to the connector base.

In certain embodiments, the electrical connection assembly further includes an electrical cable that is electrically connected to the second electrical connector and the catheter.

In some embodiments, the energy source is positioned within the system console.

In certain embodiments, the optoelectrical connector further includes (i) a plurality of ferrules, each of the plurality of ferrules being configured to retain a portion of one of the one or more energy guides, and (ii) a ferrule housing having a plurality of positioning apertures that are each configured to retain at least a portion of one of the plurality of ferrules spaced apart from one another. In some embodiments, each of the plurality of positioning apertures is larger than a diameter of the ferrule that is retained therein to allow the ferrule to move relative to the positioning aperture.

In some embodiments, the ferrule housing is adjustably positioned within the guide coupling housing so that the ferrule housing is movable relative to the guide coupling housing.

In certain embodiments, the guide coupling housing includes a console facing side; and the plurality of ferrules are recessed from the console facing side of the guide coupling housing.

In some embodiments, the optoelectrical connector further includes a sealing member that seals the connection between the guide coupling housing and the console connection aperture.

In certain embodiments, the optoelectrical connector further includes a contaminant inhibitor that is positionable about at least a portion of the guide coupling housing, the contaminant inhibitor being configured to inhibit dust and particulates from contaminating a face of each of the one or more energy guides.

In some embodiments, the optoelectrical connector further includes a locking mechanism that is configured to selectively lock the guide coupling housing in position when the guide coupling housing is being retained within the console connection aperture.

In some embodiments, the system console further includes an optical sensor and an actuator. In certain embodiments, the optical sensor is configured to sense a position of the guide coupling housing relative to the console connection aperture, and is further configured to initiate the actuator that mechanically draws the guide coupling housing into place within the console connection aperture.

In many embodiments, the catheter system further includes a balloon that is configured to be positioned substantially adjacent to the treatment site. The balloon includes a balloon wall that defines a balloon interior. The balloon is configured to retain a catheter fluid within the balloon interior. In some embodiments, each of the one or more energy guides includes a guide distal end that is configured to be positioned within the balloon interior. Each of the one or more energy guides is configured to guide the energy from the energy source through the energy guide and into the balloon interior. In certain embodiments, each of the one or more energy guides guiding the energy from the energy source into the balloon interior generates plasma in the catheter fluid within the balloon interior.

In various embodiments, at least one of the one or more energy guides includes an optical fiber; and the energy source includes a laser.

The present invention is further directed toward a method for treating a treatment site within or adjacent to a blood vessel within a body of a patient, including the steps of providing a system console including a console connection aperture; generating energy with an energy source; receiving the energy from the energy source with one or more energy guides; coupling an optoelectrical connector to a catheter, the optoelectrical connector including a guide coupling housing and at least a portion of an electrical connector assembly; retaining at least a portion of each of the one or more energy guides with the guide coupling housing of the optoelectrical connector; selectively mechanically connecting the guide coupling housing to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source; and transmitting at least one of power and data between the system console and the catheter with the electrical connector assembly when the guide coupling housing is retained within the console connection aperture.

The present invention is also directed toward a catheter system for treating a treatment site within or adjacent to a blood vessel within a body of a patient, the catheter system including a catheter; a system console including a console connection aperture, an optical sensor and an actuator; an energy source that is configured to generate energy; one or more energy guides that are configured to receive the energy from the energy source; and an optoelectrical connector that is coupled to the catheter, the optoelectrical connector including: (i) a guide coupling housing that retains at least a portion of each of the one or more energy guides, the guide coupling housing being configured to be selectively mechanically connected to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source, the optical sensor being configured to sense a position of the guide coupling housing relative to the console connection aperture, and being further configured to initiate the actuator that mechanically draws the guide coupling housing into place within the console connection aperture; (ii) at least a portion of an electrical connector assembly that is positioned adjacent to the guide coupling housing and that transmits at least one of power and data between the system console and the catheter when the guide coupling housing is retained within the console connection aperture, the electrical connection assembly including a first electrical connector that is positioned within the system console, and a second electrical connector that is positioned adjacent to the guide coupling housing, the second electrical connector being configured to interface with the first electrical connector when the guide coupling housing is retained within the console connection aperture, the second electrical connector including a connector base and a plurality of electrical connection pads that are coupled to the connector base; (iii) a plurality of ferrules, each of the plurality of ferrules being configured to retain a portion of one of the one or more energy guides; and (iv) a ferrule housing having a plurality of positioning apertures that are each configured to retain at least a portion of one of the plurality of ferrules spaced apart from one another, each of the plurality of positioning apertures being larger than a diameter of the ferrule that is retained therein to allow the ferrule to move relative to the positioning aperture, the ferrule housing being adjustably positioned within the guide coupling housing so that the ferrule housing is movable relative to the guide coupling housing.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

In various embodiments, the catheter systems and related methods disclosed herein can include a catheter configured to advance to a vascular lesion, such as a calcified vascular lesion or a fibrous vascular lesion, at a treatment site located within or adjacent to a blood vessel within a body of a patient. As used herein, the terms "treatment site," "intravascular lesion," and "vascular lesion" are used interchangeably unless otherwise noted. As such, the intravascular lesions and/or the vascular lesions are sometimes referred to herein simply as "lesions."

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings. The same or similar nomenclature and/or reference indicators will be used throughout the drawings, and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is recognized that such a development effort might be complex and time-consuming, but would nevertheless be a routine undertaking of engineering for those of ordinary skill in the art having the benefit of this disclosure.

Figure 1:
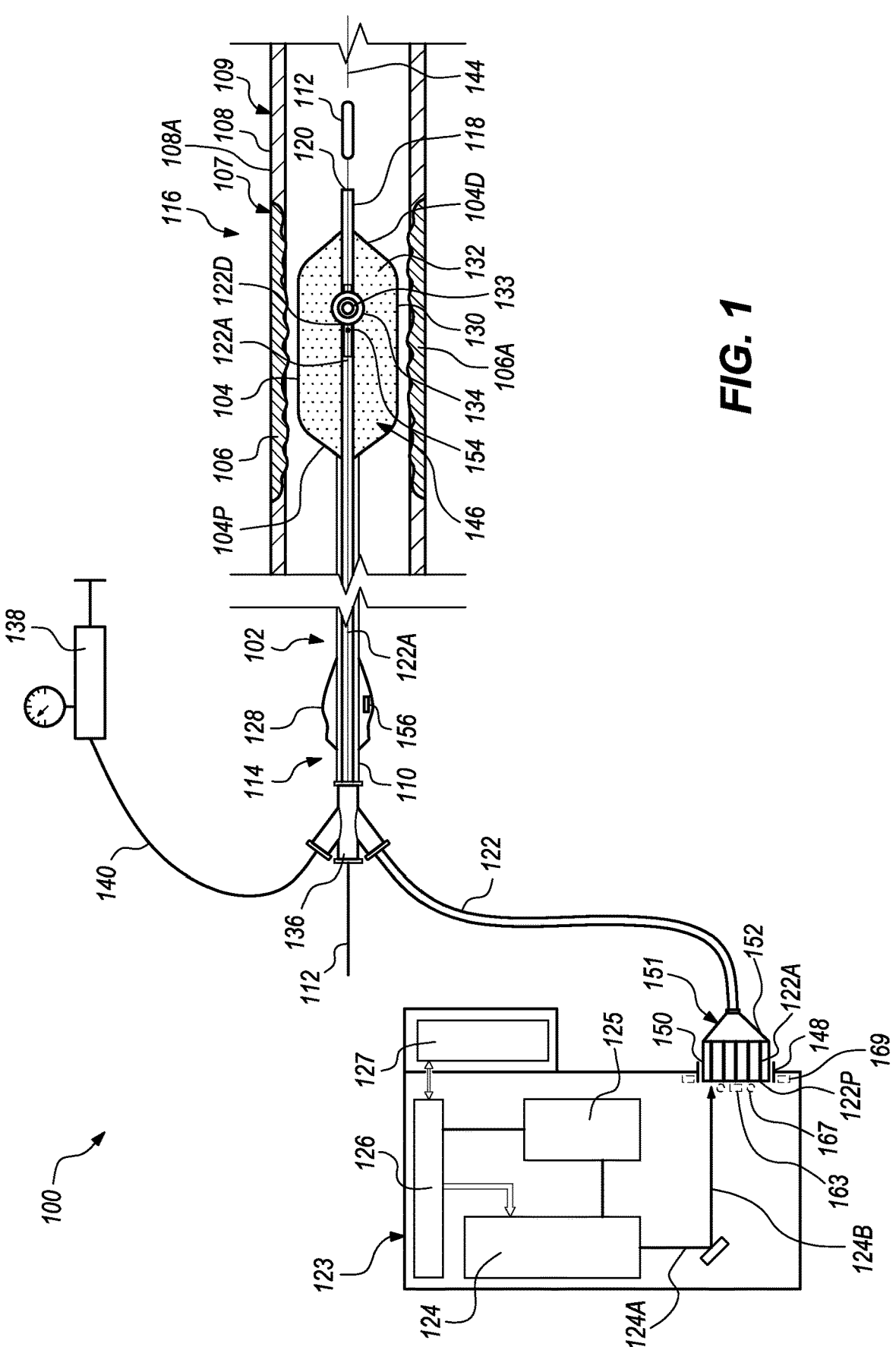
FIG. 1 is a simplified schematic cross-sectional view illustration of an embodiment of a catheter system in accordance with various embodiments.

The catheter systems disclosed herein can include many different forms. Referring now to FIG. 1, a simplified schematic cross-sectional view illustration is shown of a catheter system 100 in accordance with various embodiments. The catheter system 100 is suitable for imparting pressure waves to induce fractures in one or more vascular lesions within or adjacent to a vessel wall of a blood vessel or on or adjacent to a heart valve within a body of a patient. In the embodiment illustrated in FIG. 1, the catheter system 100 can include one or more of a catheter 102, an energy guide bundle 122 including one or more energy guides 122A, a source manifold 136, a fluid pump 138, a system console 123 including one or more of an energy source 124, a power source 125, a system controller 126, and a graphic user interface 127 (a "GUI"), and a handle assembly 128. In various embodiments, the catheter system 100 further includes an optoelectrical connector assembly 151 (also referred to herein as an "optoelectrical connector") that is configured to transmit at least one of power and data between the system console 123 and the catheter 102, as well as ensuring desired optical communication between the energy source 124 and the one or more energy guides 122A of the energy guide bundle 122. Various embodiments of the optoelectrical connector 151 will be described in greater detail herein below. Alternatively, the catheter system 100 can include more components or fewer components than those specifically illustrated and described in relation to FIG. 1.

The catheter 102 is configured to move to the treatment site 106 within or adjacent to a vessel wall 108A of a blood vessel 108 within a body 107 of a patient 109. The treatment site 106 can include one or more vascular lesions 106A, such as calcified vascular lesions, for example. Additionally, or in the alternative, the treatment site 106 can include vascular lesions 106A, such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter 102 and/or the catheter shaft 110 can also include a guidewire lumen 118, which is configured to move over the guidewire 112. As utilized herein, the guidewire lumen 118 defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a catheter fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106. It is appreciated that although FIG. 1 illustrates the balloon wall 130 of the balloon 104 being shown spaced apart from the treatment site 106 of the blood vessel 108 when in the inflated state, this is done for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient 109 when in the deflated state. In some embodiments, the balloons 104 are made from silicone. In other embodiments, the balloon 104 can be made from materials such as polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. Alternatively, the balloon 104 can have another suitable diameter (in the inflated state).

In various non-exclusive alternative embodiments, the balloon 104 can have a length ranging from at least three mm to 300 mm, which can be selected based on the size and/or length of the vascular lesions 106A at the treatment site 106.

The balloon 104 can be inflated to inflation pressures of between approximately one atmosphere (atm) and 70 atm. Alternatively, the balloon 104 can be inflated to other suitable inflation pressures.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug-eluting coating or a drug-eluting stent structure. The drug-eluting coating or drug-eluting stent can include one or more therapeutic agents, including anti-inflammatory agents, anti-neoplastic agents, anti-angiogenic agents, and the like.

The catheter fluid 132 can be a liquid or a gas. Some examples of the catheter fluid 132 suitable for use can include, but are not limited to one or more of water, saline, contrast medium, fluorocarbons, perfluorocarbons, gases, such as carbon dioxide, or any other suitable catheter fluid 132. In some embodiments, the catheter fluid 132 can be used as a base inflation fluid. In some embodiments, the catheter fluid 132 can include a mixture of saline to contrast medium in a volume ratio of approximately 50:50. In other embodiments, the catheter fluid 132 can include a mixture of saline to contrast medium in a volume ratio of approximately 25:75. In still other embodiments, the catheter fluid 132 can include a mixture of saline to contrast medium in a volume ratio of approximately 75:25. However, it is understood that any suitable ratio of saline to contrast medium can be used. The catheter fluid 132 can be tailored on the basis of composition, viscosity, and the like so that the rate of travel of the pressure waves is appropriately manipulated. In certain embodiments, the catheter fluids 132 suitable for use are biocompatible. A volume of catheter fluid 132 can be tailored by the chosen energy source 124 and the type of catheter fluid 132 used.

In some embodiments, the contrast agents used in the contrast media can include, but are not to be limited to, iodine-based contrast agents, such as ionic or non-ionic iodine-based contrast agents. In other embodiments, non-iodine-based contrast agents can be used.

The catheter fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Alternatively, the catheter fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers usable in the catheter system 100 can include neodymium:yttrium-aluminum-garnet (Nd:YAG–emission maximum=1064 nm) lasers, holmium:YAG (Ho:YAG–emission maximum =2.1 μm) lasers, or erbium:YAG (Er:YAG–emission maximum=2.94 μm) lasers. In some embodiments, the absorptive agents can be water-soluble. In other embodiments, the absorptive agents are not water-soluble. In some embodiments, the absorptive agents used in the catheter fluids 132 can be tailored to match the peak emission of the energy source 124.

The catheter shaft 110 of the catheter 102 can be coupled to the one or more energy guides 122A of the energy guide bundle 122, which are in optical communication with the energy source 124 via the optoelectrical connector 151. The energy guide(s) 122A can be disposed along the catheter shaft 110 and within the balloon 104. In some embodiments, each energy guide 122A can be an optical fiber, and the energy source 124 can be a laser. The energy source 124 can be in optical communication with the energy guides 122A at the proximal portion 114 of the catheter system 100, such as where the energy guides 122A are selectively, mechanically coupled into the system console 123 via the optoelectrical connector 151.

In some embodiments, the catheter shaft 110 can be coupled to multiple energy guides 122A, such as a first energy guide, a second energy guide, a third energy guide, etc., which can be disposed at any suitable positions about and/or relative to the guidewire lumen 118 and/or the catheter shaft 110. In certain non-exclusive embodiments, the catheter shaft 110 can be coupled to two energy guides 122A, three energy guides 122A, four energy guides 122A, five energy guides 122A, six energy guides 122A, eight energy guides 122A or ten energy guides 122A, which can be uniformly spaced apart from one another about the circumference of the guidewire lumen 118 and/or the catheter shaft 110. Alternatively, multiple energy guides 122A need not be uniformly spaced apart from one another about the circumference of the guidewire lumen 118 and/or the catheter shaft 110. More particularly, it is further appreciated that the energy guides 122A can be disposed uniformly or non-uniformly about the guidewire lumen 118 and/or the catheter shaft 110 to achieve the desired effect in the desired locations.

The catheter system 100 and/or the energy guide bundle 122 can include any number of energy guides 122A in optical communication with the energy source 124 at the proximal portion 114 (via the optoelectrical connector 151), and with the catheter fluid 132 within the balloon interior 146 of the balloon 104 at the distal portion 116. For example, in some embodiments, the catheter system 100 and/or the energy guide bundle 122 can include from one energy guide 122A to 30 energy guides 122A. Alternatively, in other embodiments, the catheter system 100 and/or the energy guide bundle 122 can include greater than 30 energy guides 122A.

The energy guides 122A can have any suitable design for purposes of generating plasma and/or pressure waves in the catheter fluid 132 within the balloon interior 146. Thus, the general description of the energy guides 122A as light guides is not intended to be limiting in any manner, except for as set forth in the claims appended hereto. More particularly, although the catheter systems 100 are often described with the energy source 124 as a light source and the one or more energy guides 122A as light guides, the catheter system 100 can alternatively include any suitable energy source 124 and energy guides 122A for purposes of generating the desired plasma in the catheter fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves in the catheter fluid 132 that are utilized to provide the fracture force onto the vascular lesions 106A at the treatment site 106. Still alternatively, the energy source 124 and/or the energy guides 122A can have another suitable design and/or configuration.

In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide energy along its length from a guide proximal end 122P to the guide distal end 122D having at least one optical window (not shown) that is positioned within the balloon interior 146.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A can be disposed within one or more energy guide lumens within the catheter shaft 110.

The energy guides 122A can be disposed at any suitable positions about the circumference of the guidewire lumen 118 and/or the catheter shaft 110, and the guide distal end 122D of each of the energy guides 122A can be disposed at any suitable longitudinal position relative to the length of the balloon 104 and/or relative to the length of the guidewire lumen 118 to more effectively and more precisely impart pressure waves for purposes of disrupting the vascular lesions 106A at the treatment site 106.

In certain embodiments, the energy guides 122A can include one or more photoacoustic transducers 154, where each photoacoustic transducer 154 can be in optical communication with the energy guide 122A within which it is disposed. In some embodiments, the photoacoustic transducers 154 can be in optical communication with the guide distal end 122D of the energy guide 122A. In such embodiments, the photoacoustic transducers 154 can have a shape that corresponds with and/or conforms to the guide distal end 122D of the energy guide 122A.

The photoacoustic transducer 154 is configured to convert light energy into an acoustic wave at or near the guide distal end 122D of the energy guide 122A. The direction of the acoustic wave can be tailored by changing an angle of the guide distal end 122D of the energy guide 122A.

In certain embodiments, the photoacoustic transducers 154 disposed at the guide distal end 122D of the energy guide 122A can assume the same shape as the guide distal end 122D of the energy guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The energy guide 122A can further include additional photoacoustic transducers 154 disposed along one or more side surfaces of the length of the energy guide 122A.

In some embodiments, the energy guides 122A can further include one or more diverting structures or "diverters" (not shown in FIG. 1), such as within the energy guide 122A and/or near the guide distal end 122D of the energy guide 122A. Such diverting structures are configured to direct energy from the energy guide 122A away from its axial path and toward a side surface which can be located at or near the guide distal end 122D of the energy guide 122A, before the energy is directed toward the balloon wall 130. The energy guides 122A can each include one or more optical windows disposed along the longitudinal or circumferential surfaces of each energy guide 122A and in optical communication with a diverting structure. The optical windows can include a portion of the energy guide 122A that allows energy to exit the energy guide 122A from within the energy guide 122A, such as a portion of the energy guide 122A lacking a cladding material on or about the energy guide 122A.

Examples of the diverting structures suitable for use include a reflecting element, a refracting element, and a fiber diffuser. The diverting structures suitable for focusing energy away from the tip of the energy guides 122A can include, but are not to be limited to, those having a convex surface, a gradient-index (GRIN) lens, and a mirror focus lens. Upon contact with the diverting structure, the energy is diverted within the energy guide 122A to one or more of a plasma generator 133 and the photoacoustic transducer 154 that is in optical communication with a side surface and/or an optical window of the energy guide 122A.

The source manifold 136 can be positioned at or near the proximal portion 114 of the catheter system 100. The source manifold 136 can include one or more proximal end openings that can receive the plurality of energy guides 122A of the energy guide bundle 122, the guidewire 112, and/or an inflation conduit 140 that is coupled in fluid communication with the fluid pump 138. The catheter system 100 can also include the fluid pump 138 that is configured to inflate the balloon 104 with the catheter fluid 132 as needed.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided at any suitable location within the catheter system 100 without the specific need for the system console 123.

As shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a "socket" or a "console receptacle") by which the energy guide bundle 122 is mechanically coupled to the system console 123. In such embodiments, the energy guide bundle 122 can include and/or incorporate the optoelectrical connector 151 having a guide coupling housing 150 (also sometimes referred to generally as a "connector housing") that houses a portion, such as the guide proximal end 122P, of each of the energy guides 122A. At least a portion of the guide coupling housing 150 is configured to fit and be selectively retained within the console connection aperture 148 to provide the mechanical coupling between the energy guide bundle 122 and the system console 123.

As described in greater detail herein below, in various embodiments, the optoelectrical connector 151 is configured to ensure proper alignment and coupling of the energy guide bundle 122 and/or each of the one or more energy guides 122A to the system console 123 so that energy from the energy source 124 is more precisely and accurately directed into the guide proximal end 122P of each of the one or more energy guides 122A before such energy is guided by the one or more energy guides 122A into the balloon interior 146. In certain embodiments, the system console 123 can also be configured to include certain features or components, such as at least one optical sensor 167 (illustrated in phantom) that is usable in conjunction with at least one actuator 169 (illustrated in phantom), that further enable the precise alignment and coupling of the energy bundle 122 and/or each of the one or more energy guides 122A to the system console 123 and/or energy from the energy source 124 that is retained therein.

As also described in greater detail herein below, in many embodiments, the optoelectrical connector 151 is further configured to ensure proper electrical connection between the system console 123, and thus the power source 125, and various other components of the catheter system 100. More particularly, in some embodiments, the system console 123 can include a first electrical connector 163 (illustrated in phantom) that is configured to interface with a second electrical connector 465 (illustrated, for example, in FIG. 4) that is positioned within and/or adjacent to the guide coupling housing 150, and/or incorporated within the optoelectrical connector 151, to ensure power and data can be effectively transmitted between the system console 123 and the catheter 102. As referred to herein, the first electrical connector 163 and the second electrical connector 465 can sometimes be referred to herein individually and/or collectively as an "electrical connection assembly". In some embodiments, the electrical connection assembly can also include an electrical cable 386 (illustrated in FIG. 3) that can be coupled to the second electrical connector 465 for further enhancing the transmission of power and data between the system console 123 and various other components of the catheter system 100.

It is appreciated that the reference to the first electrical connector 163 and the second electrical connector 465 as part of the electrical connection assembly is merely for convenience, and either electrical connector can be referred to as the "first electrical connector" and/or the "second electrical connector."

The energy guide bundle 122 and/or the optoelectrical connector 151 can also include a guide bundler 152 (or "shell") that provides strain relief as it brings each of the individual energy guides 122A closer together so that the energy guides 122A and/or the energy guide bundle 122 can be in a more compact form as it extends with the catheter 102 into the blood vessel 108 during use of the catheter system 100.

The energy source 124 can be selectively and/or alternatively coupled in optical communication with each of the energy guides 122A, such as to the guide proximal end 122P of each of the energy guides 122A, in the energy guide bundle 122. In particular, the energy source 124 is configured to generate energy in the form of a source beam 124A, such as a pulsed source beam, that can be selectively and/or alternatively directed to and received by each of the properly aligned energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, the energy source 124 can be configured to provide sub-millisecond pulses of energy from the energy source 124 that are focused onto a small spot in order to couple it into the guide proximal end 122P of the energy guide 122A. Such pulses of energy are then directed and/or guided along the energy guides 122A to a location within the balloon interior 146 of the balloon 104, thereby inducing plasma formation in the catheter fluid 132 within the balloon interior 146 of the balloon 104, such as via the plasma generator 133 that can be located at or near the guide distal end 122D of the energy guide 122A. In particular, the energy emitted at the guide distal end 122D of the energy guide 122A is directed toward and impinges on and energizes the plasma generator 133 to form the plasma in the catheter fluid 132 within the balloon interior 146. The plasma formation causes rapid bubble formation, and imparts pressure waves upon the treatment site 106. An exemplary plasma-induced bubble 134 is illustrated in FIG. 1.

In various non-exclusive alternative embodiments, the sub-millisecond pulses of energy from the energy source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of energy can be delivered to the treatment site 106 at a frequency that can be greater than 5000 Hz or less than one Hz, or any other suitable range of frequencies.

It is appreciated that although the energy source 124 is typically utilized to provide pulses of energy, the energy source 124 can still be described as providing a single source beam 124A, such as a single pulsed source beam.

The energy sources 124 suitable for use can include various types of light sources including lasers and lamps. Alternatively, the energy sources 124 can include any suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the catheter fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter systems 100 can include those capable of producing light at wavelengths of from at least 750 nm to 2000 nm. In other embodiments, the energy sources 124 can include those capable of producing light at wavelengths from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz.

In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

In still other embodiments, the energy source 124 can include a plurality of lasers that are grouped together in series. In yet other embodiments, the energy source 124 can include one or more low energy lasers that are fed into a high energy amplifier, such as a master oscillator power amplifier (MOPA). In still yet other embodiments, the energy source 124 can include a plurality of lasers that can be combined in parallel or in series to provide the energy needed to create the plasma bubble 134 in the catheter fluid 132.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter systems 100 can generate pressure waves having maximum pressures in the range of at least approximately two MPa to 50 MPa, at least approximately two MPa to 30 MPa, or approximately at least 15 MPa to 25 MPa.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide the necessary power to each of the energy source 124, the system controller 126, the GUI 127, and the handle assembly 128. The power source 125 can have any suitable design for such purposes.

The system controller 126 is electrically coupled to and receives power from the power source 125. The system controller 126 is coupled to and is configured to control the operation of each of the energy source 124 and the GUI 127. The system controller 126 can include one or more processors or circuits for purposes of controlling the operation of at least the energy source 124 and the GUI 127. For example, the system controller 126 can control the energy source 124 for generating pulses of energy as desired and/or at any desired firing rate.

The system controller 126 can also be configured to control the operation of other components of the catheter system 100, such as the positioning of the catheter 102 adjacent to the treatment site 106, the inflation of the balloon 104 with the catheter fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. The GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during, and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during the use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications, and/or desires of the user or operator.

As shown in FIG. 1, the handle assembly 128 can be positioned at or near the proximal portion 114 of the catheter system 100. In this embodiment, the handle assembly 128 is coupled to the balloon 104 and positioned separately from the balloon 104. Alternatively, the handle assembly 128 can be positioned at another suitable location.

The handle assembly 128 is attached to the catheter shaft 110 and is handled and used by the user or operator to operate, position, and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, and the GUI 127.

In some embodiments, the handle assembly 128 can integrate and/or include at least a portion of the system controller 126 within an interior of the handle assembly 128. For example, as shown, in certain such embodiments, the handle assembly 128 can include circuitry 156, which is electrically coupled between catheter electronics and the system console 123, and which can form at least a portion of the system controller 126. In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, such as within the system console 123. It is understood that the handle assembly 128 can include fewer or additional components than those specifically illustrated and described herein.

The catheter system 100 can also include the fluid pump 138 that is configured to inflate the balloon 104 with the catheter fluid 132 as needed.

As with all embodiments illustrated and described herein, various structures may be omitted from the figures for clarity and ease of understanding. Further, the figures may include certain structures that can be omitted without deviating from the intent and scope of the invention.

Figure 2:
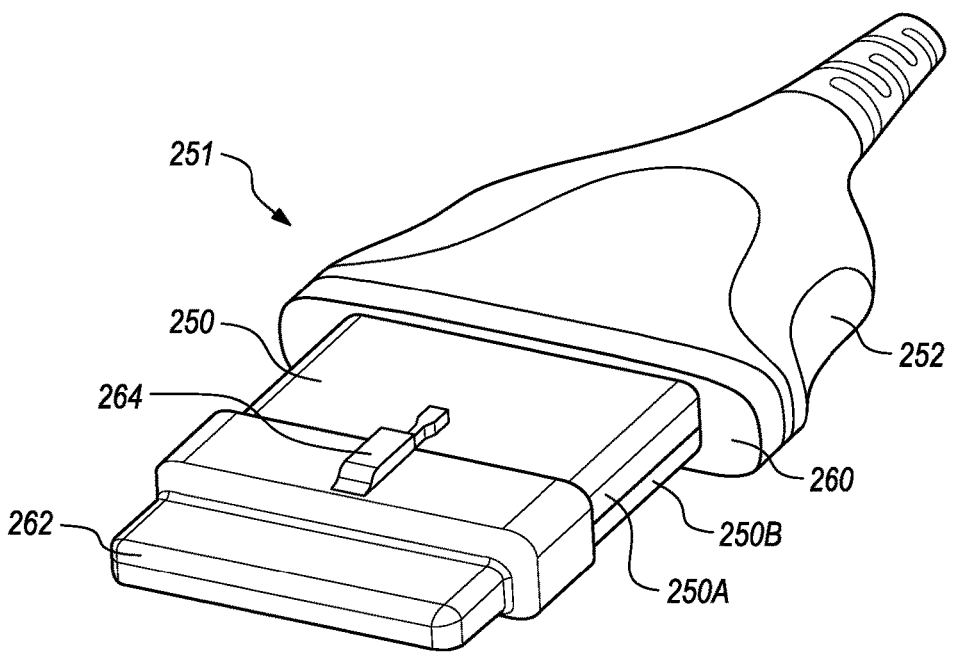
FIG. 2 is a simplified perspective view illustration of an embodiment of an optoelectrical connector assembly having features of the present invention that can be included as part of the catheter system of FIG. 1.

FIG. 2 is a simplified perspective view illustration of an embodiment of an optoelectrical connector assembly 251 having features of the present invention that can be included as part of the catheter system 100 of FIG. 1.

The design of the optoelectrical connector 251 can be varied. As shown, FIG. 2 illustrates various external components and features that can be included in various embodiments of the optoelectrical connector 251. In particular, as illustrated, the optoelectrical connector 251 can include one or more of a guide coupling (or connector) housing 250, a guide bundler 252, a sealing member 260, a contaminant inhibitor 262, and a locking mechanism 264. Alternatively, the optoelectrical connector 251 can include greater or fewer external components than those specifically noted.

One primary purpose of the optoelectrical connector 251 is to provide a means to connect ferrules 366 (illustrated, for example, in FIG. 3) located within it, and thus the energy guides 122A (illustrated in FIG. 1) that are positioned at least partially within the ferrules 366, into the console connection aperture 148 (or "console receptacle," illustrated in FIG. 1). Thus, with the optoelectrical connector 251, and the ferrules 366 and energy guides 122A retained at least partially therein, connected and aligned more precisely within the console connection aperture 148 of the system console 123 (illustrated in FIG. 1), energy from the energy source 124 (illustrated in FIG. 1) can be effectively and selectively coupled into each of the one or more energy guides 122A.

Another primary purpose of the optoelectrical connector 251 is to ensure proper electrical connections are established between the system console 123 and the remainder of the catheter system 100. In particular, in various embodiments, the system console 123 can include the first electrical connector 163 (illustrated in FIG. 1), and the optoelectrical connector 251 can include the second electrical connector 465 (illustrated, for example, in FIG. 4) that are configured to interface with one another to ensure power and data can be effectively transmitted between the system console 123 and the catheter 102 (illustrated in FIG. 1). It is appreciated that the first electrical connector 163 and the second electrical connector 465 can have any suitable design for purposes of effectively ensuring that power and data can be effectively transmitted between the system console 123 and the catheter 102.

In various embodiments, the optoelectrical connector 251 and/or the system console 123 (illustrated in FIG. 1) can include certain features or components to better ensure a more precisely aligned connection therebetween. For example, in some embodiments, the optoelectrical connector 251 can include (i) the ferrules 366 that are allowed to float relative to and/or within a ferrule housing 370 (illustrated in FIG. 3) by the ferrule housing 370 having positioning apertures 576 (illustrated in FIG. 5) within which at least a portion of the ferrules 366 is retained that is slightly larger than the diameter of the ferrules 366; (ii) the ferrule housing 370 that is allowed to float relative to the guide coupling housing 250 by selectively moving the ferrule housing 370 (up-and-down and/or side-to-side) relative to the guide coupling housing 250 as necessary; (iii) a position compensator 374 (illustrated in FIG. 3) that is configured to provide a spring force to keep the ferrules 366 in an aligned position, while still allowing play within the ferrule housing 370; and (iv) a resilient plate 372 (illustrated in FIG. 3) that is configured to control the floating of the ferrule housing 370 within the guide coupling housing 250. In certain embodiments, the system console 123 can include one or more optical sensors 167 (illustrated in FIG. 1) that are configured to sense a position of the optoelectrical connector 251 and/or the guide coupling housing 250 relative to the system console 123 and/or the console connection aperture 148. Based on the sensed position of the optoelectrical connector 251 and/or the guide coupling housing 250 relative to the system console 123 and/or the console connection aperture 148, an actuator 169 (illustrated in FIG. 1) can then be initiated that mechanically draws the optoelectrical connector 251 accurately into place within the console connection aperture 148.

The guide coupling housing 250 is configured to house a portion of each of the energy guides 122A, such as the guide proximal end 122P, and to fit and be selectively retained within the console connection aperture 148 to provide the mechanical coupling between the energy guide bundle 122 (illustrated in FIG. 1) and the system console 123. The design of the guide coupling housing 250 can be varied to suit the requirements of the catheter system 100 and/or the optoelectrical connector 251. In certain embodiments, the guide coupling housing 250 can be formed from multiple housing members, such as a first housing member 250A and a second housing member 250B, that can be selectively coupled together to retain various internal components of the optoelectrical connector 251 effectively within a housing cavity 368 (illustrated in FIG. 3) defined therein. In one embodiment, each of the first housing member 250A and the second housing member 250B can form one-half of the guide coupling housing 250 (such as a top half and a corresponding bottom half in one non-exclusive embodiment), with each half being substantially similar to the other half. It is appreciated that the housing members 250A, 250B can be selectively coupled together in any suitable manner. Alternatively, the guide coupling housing 250 can have another suitable design. For example, in certain alternative embodiments, the guide coupling housing 250 can have more than two housing members or only a single housing member.

It is appreciated that the guide coupling housing 250 and/or the individual housing members 250A, 250B can be formed from any suitable materials that provide an effective housing to protect the various internal components retained therein. Various internal components of the optoelectrical connector 251 are illustrated and described herein below in relation to FIG. 3.

The guide bundler 252 is configured to provide strain relief as it brings each of the individual energy guides 122A closer together so that the energy guides 122A and/or the energy guide bundle 122 can be in a more compact form as it extends with the catheter 102 (illustrated in FIG. 1) into the blood vessel 108 (illustrated in FIG. 1) during use of the catheter system 100. Certain internal components that can be included within the guide bundler 252 for purposes of providing strain relief as it brings the energy guides 122A closer together within the energy guide bundle 122 are also illustrated and described herein below in relation to FIG. 3.

During the use of the catheter system 100, it is desired to limit the amount of dust and other particulates that may otherwise contaminate a guide face of the guide proximal end 122P (illustrated in FIG. 1) of each of the one or more energy guides 122A.

The sealing member 260 is configured to seal the connection between the optoelectrical connector 251 and the system console 123 when the guide coupling housing 250 is inserted into and selectively retained within the console connection aperture 148. With such design, the sealing member 260, which can be provided in the form of a face gasket in one non-exclusive embodiment, can help to limit the amount of dust and other particulates that may otherwise be introduced into the guide coupling housing 250 and/or the guide coupler 252. In some embodiments, the sealing member 260 can be formed from a resilient material that can effectively provide a sealed connection between the guide coupling housing 250 and the console connection aperture 148. Alternatively, the sealing member 260 can be formed from another suitable material.

The contaminant inhibitor 262 is similarly configured to limit the amount of dust or other particulates that may otherwise contaminate the guide face of each of the one or more energy guides 122A. More particularly, as shown, the contaminant inhibitor 262 can be configured to be positioned about and/or near a portion of the guide coupling housing 250 within which the ferrules 366, and thus the guide proximal end 122P of each of the energy guides 122A, are retained. The contaminant inhibitor 262 can have any suitable design which is configured to inhibit the introduction of dust and other particulates into the guide coupling housing 250 while still permitting energy from the energy source 124 to be coupled into the guide proximal end 122P of each of the one or more energy guides 122A.

In certain embodiments, the contaminant inhibitor 262 can be disposable such that when it gets sufficiently contaminated with dust and other particulates, the contaminant inhibitor 262 can be simply thrown away. In other embodiments, the contaminant inhibitor 262 can be reusable, such that it can be selectively removed from the guide coupling housing 250 and cleaned, and then again selectively coupled to the guide coupling housing 250 for additional use.

The locking mechanism 264 is configured to selectively lock the optoelectrical connector 251 in position when it is coupled into the console connection aperture 148. More specifically, during use of the catheter system 100, as the optoelectrical connector 251 is inserted into the console connection aperture 148 of the system console 123, the optical sensors 167 register it and initiate the actuator 169 that mechanically draws the optoelectrical connector 251 into place and locks it in position. The locking mechanism 264 provides an effective means to thus lock the optoelectrical connector 251 in such a position where the optoelectrical connector 251 has been inserted into the console connection aperture 148 so that it can be selectively and securely retained therein.

Figure 3:
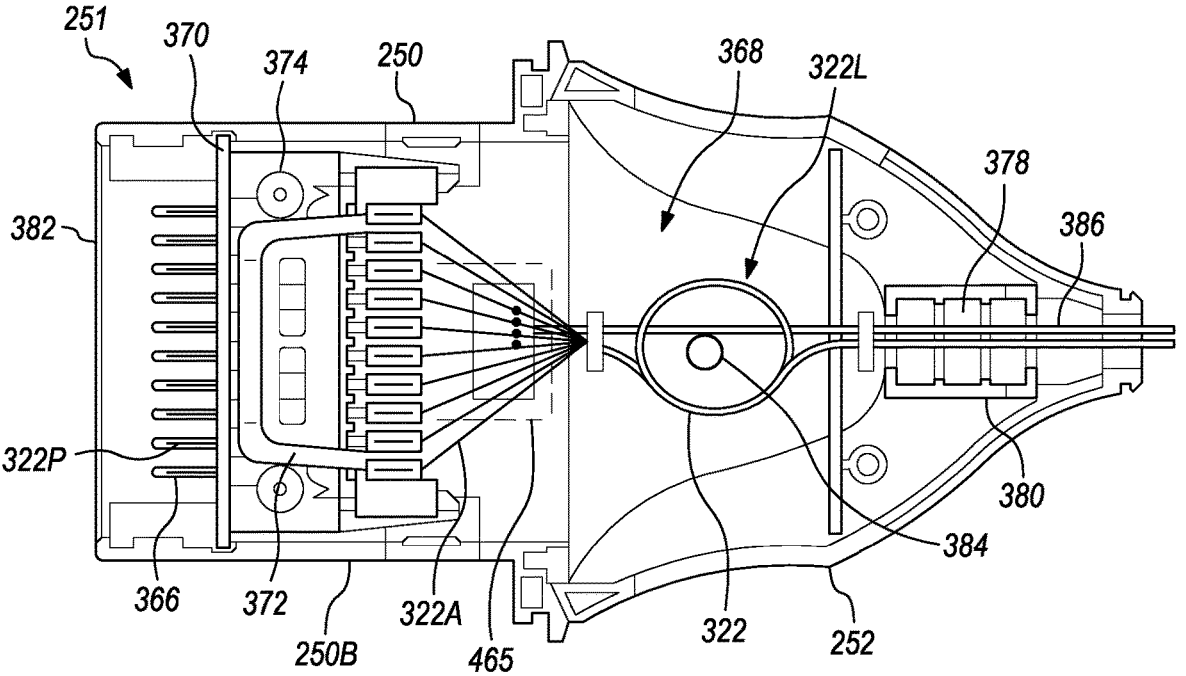
FIG. 3 is a simplified top view illustration of a portion of the optoelectrical connector assembly illustrated in FIG. 2.

FIG. 3 is a simplified top view illustration of a portion of the optoelectrical connector 251 illustrated in FIG. 2. More specifically, FIG. 3 illustrates various internal components and features that can be included in various embodiments of the optoelectrical connector 251. As shown in FIG. 3, in various embodiments, the optoelectrical connector 251 can internally include within the guide coupling housing 250 one or more of a plurality of ferrules 366, a ferrule housing 370, a portion of the one or more energy guides 322A, a resilient plate 372, at least one position compensator 374 (such as a silicone gasket in one non-exclusive embodiment), and at least a portion of the guide bundler 252. It is appreciated that only the second housing member 250B of the guide coupling housing 250 is visible in FIG. 3 so that the other noted components can be clearly seen positioned within the housing cavity 368 that is defined within the guide coupling housing 250 and/or within the guide bundler 252.

As utilized herein, a "ferrule" is a component in fiber optics used for protecting and aligning a stripped end of the energy guide 322A (or optical fiber). During use, the energy guide 322A is inserted into the thin structure of the ferrule 366 and can be provided with an adhesive (not shown) to prevent contamination as well as to give it long-term mechanical strength. The ferrules 366 can be formed from any suitable materials for purposes of providing the desired contamination protection for the stripped guide proximal end 322P of the energy guides 322A as well as the enhanced, long-term mechanical strength.

The optoelectrical connector 251 can include any suitable number of ferrules 366 within the housing cavity 368 as defined by the guide coupling housing 250, depending on the number of energy guides 322A that are to be optically connected to the energy source 124 (illustrated in FIG. 1). For example, in one non-exclusive embodiment, as shown in FIG. 3, the optoelectrical connector 251 can include ten ferrules 366 that are each configured to retain and protect a portion, such as the guide proximal end 322P, of one of the one or more energy guides 322A. Thus, in such embodiment, the energy guide bundle 322 can include up to ten energy guides 322A. Alternatively, the optoelectrical connector 251 can include greater than ten or less than ten ferrules 366.

As further shown in FIG. 3, in some embodiments, the ferrules 366 are positioned in a manner within the guide coupling housing 250 such that the ferrules 366 are recessed relative to a console facing side 382 of the guide coupling housing 250. With the ferrules 366 being recessed from the console facing side 382 of the guide coupling housing 250, the optoelectrical connector 251 is configured to help ensure that fingers or other objects do not come into contact with faces of the energy guides 322A, at the guide proximal end 322P of the energy guides 322A, which could otherwise lead to undesired contamination.

The ferrules 366 can be recessed any desired distance from the console facing side 382 of the guide coupling housing 250 depending on the specific design requirements of the optoelectrical connector 251 and/or the catheter system 100.

The ferrule housing 370 is configured to provide a housing for the ferrules 366 so that the ferrules 366 can be moved and positioned collectively relative to the energy from the energy source 124. The ferrule housing 370 further enables the ferrules 366 to be maintained spaced apart a desired distance from one another, so that the guide proximal end 322P of each of the energy guides 322A can be properly aligned to accurately receive energy from the energy source 124. At the side of the guide coupling housing 250 that faces the console connection aperture 148 (illustrated in FIG. 1) of the system console 123 (illustrated in FIG. 1), i.e., the left side in FIG. 3, faces of the ferrules 366 are exposed. In certain embodiments, the ferrules 366 are allowed to float significantly within and/or relative to the ferrule housing 370, and the ferrule housing 370 is allowed to float within and/or relative to the guide coupling housing 250, to allow for the ferrules 366, and thus the guide proximal end 322P of the energy guides 322A, to be easily and precisely adjusted so as to more accurately line up with the console connection aperture 148 of the system console 123.

The resilient plate 372, such as a spring plate in certain embodiments, is configured to control the floating of the ferrule housing 370 within and/or relative to the guide coupling housing 250. More particularly, as the ferrule housing 370 is allowed to float within the guide coupling housing 250, it is desired that the ferrule housing 370 does not just float loosely without control within the guide coupling housing 250. The resilient plate 372 provides a biasing force that allows the ferrule housing 370 to float within the guide coupling housing 250 while enabling the ferrule housing 370 to be resiliently maintained in position within the guide coupling housing 250 once a desired positioning is accurately determined.

At least one position compensator 374, such as silicone gaskets in certain non-exclusive embodiments, is configured to provide a spring force to keep the ferrules 366 in an aligned position, while still allowing play within the ferrule housing 370. However, if the ferrule housing 370 needs to adjust to accommodate fit with the ferrules 366 relative to the console connection aperture 148 and/or the energy from the energy source 124, then the ferrule housing 370 can be moved to accommodate such an adjusted position. Without the at least one position compensator 374, the ferrules 366 could seize with the console connection aperture 148, due to fit interference.

The optoelectrical connector 251 can include any suitable number of position compensators 374. For example, in one non-exclusive embodiment, the optoelectrical connector 251 can include four position compensators 374. Alternatively, in other embodiments, the optoelectrical connector 251 can include greater than four or less than four position compensators 374.

As noted above, the guide bundler 252 is configured to provide strain relief as it brings each of the individual energy guides 322A closer together so that the energy guides 322A and/or the energy guide bundle 322 can be in a more compact form as it extends with the catheter 102 (illustrated in FIG. 1) into the blood vessel 108 (illustrated in FIG. 1) during use of the catheter system 100 (illustrated in FIG. 1). The design of the guide bundler 252 can be varied. For example, as shown in FIG. 3, in certain embodiments, the guide bundler 252 can include a shaft jacket 378 within which a portion of all of the energy guides 322A are maintained as the energy guide bundle 322 extends with the catheter 102 toward the balloon 104 (illustrated in FIG. 1). The guide bundler 252 can also include a locking crimp 380 that is configured to tightly bunch the energy guides together in a controlled manner to form the energy guide bundle 322.

As shown, FIG. 3 also illustrates the routing of the energy guides 322A as they extend through the guide coupling housing 250 of the optoelectrical connector 251. More specifically, the guide proximal end 322P of each of the energy guides 322A is positioned within one of the ferrules 366 near the side of the guide coupling housing 250 that faces the console connection aperture 148 (illustrated in FIG. 1) of the system console 123, with the energy guides 322A being positioned at a desired spacing relative to one another. The energy guides 322A then extend through the guide coupling housing 250 to where they are brought closer together, or bundled together, at the guide bundler 252. The energy guide bundle 322, with a portion of the energy guides 322A positioned within the shaft jacket 378, then extends with the catheter 102 toward the balloon 104.

In certain embodiments, as illustrated in FIG. 3, the energy guides 322A can include a service loop 322L. Movement of the energy guides 322A throughout the catheter system 100 can result in alternating periods of slack and tension on the energy guides 322A, which can cause axial and longitudinal movement of the guides and cables. Such movement may result in the undesired cramping and/or twisting of the energy guides 322A of the catheter system 300 and may cause the degradation of the energy guides 322A. Thus, the inclusion of the service loop 322L can help to inhibit any undesired cramping and/or twisting of the energy guides 322A as the service loop 322L helps to minimize the alternating periods of slack and tension on the energy guides 322A.

In some embodiments, as illustrated, the service loop 322L can loop around a service loop guide 384. For example, in certain non-exclusive embodiments, the energy guides 322A can loop greater than approximately 5 degrees and less than approximately 1080 degrees about the service loop guide 384. More particularly, the energy guides 322A can loop approximately 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, 180 degrees, 185 degrees, 190 degrees, 195 degrees, 200 degrees, 205 degrees, 210 degrees, 215 degrees, 220 degrees, 225 degrees, 230 degrees, 235 degrees, 240 degrees, 245 degrees, 250 degrees, 255 degrees, 260 degrees, 265 degrees, 270 degrees, 275 degrees, 280 degrees, 285 degrees, 290 degrees, 295 degrees, 300 degrees, 305 degrees, 310 degrees, 315 degrees, 320 degrees, 325 degrees, 330 degrees, 335 degrees, 340 degrees, 345 degrees, 350 degrees, 355 degrees, 360 degrees, 365 degrees, 370 degrees, 375 degrees, 380 degrees, 385 degrees, 390 degrees, 395 degrees, 400 degrees, 405 degrees, 410 degrees, 415 degrees, 420 degrees, 425 degrees, 430 degrees, 435 degrees, 440 degrees, 445 degrees, 450 degrees, 455 degrees, 460 degrees, 465 degrees, 470 degrees, 475 degrees, 480 degrees, 485 degrees, 490 degrees, 495 degrees, 500 degrees, 505 degrees, 510 degrees, 515 degrees, 520 degrees, 525 degrees, 530 degrees, 535 degrees, 540 degrees, 545 degrees, 550 degrees, 555 degrees, 560 degrees, 565 degrees, 570 degrees, 575 degrees, 580 degrees, 585 degrees, 590 degrees, 595 degrees, 600 degrees, 605 degrees, 610 degrees, 615 degrees, 620 degrees, 625 degrees, 630 degrees, 635 degrees, 640 degrees, 645 degrees, 650 degrees, 655 degrees, 660 degrees, 665 degrees, 670 degrees, 675 degrees, 680 degrees, 685 degrees, 690 degrees, 695 degrees, 700 degrees, 705 degrees, 710 degrees, 715 degrees, 720 degrees, 725 degrees, 730 degrees, 735 degrees, 740 degrees, 745 degrees, 750 degrees, 755 degrees, 760 degrees, 765 degrees, 770 degrees, 775 degrees, 780 degrees, 785 degrees, 790 degrees, 795 degrees, 800 degrees, 805 degrees, 810 degrees, 815 degrees, 820 degrees, 825 degrees, 830 degrees, 835 degrees, 840 degrees, 845 degrees, 850 degrees, 855 degrees, 860 degrees, 865 degrees, 870 degrees, 875 degrees, 880 degrees, 885 degrees, 890 degrees, 895 degrees, 900 degrees, 905 degrees, 910 degrees, 915 degrees, 920 degrees, 925 degrees, 930 degrees, 935 degrees, 940 degrees, 945 degrees, 950 degrees, 955 degrees, 960 degrees, 965 degrees, 970 degrees, 975 degrees, 980 degrees, 985 degrees, 990 degrees, 995 degrees, 1000 degrees, 1005 degrees, 1010 degrees, 1015 degrees, 1020 degrees, 1025 degrees, 1030 degrees, 1035 degrees, 1040 degrees, 1045 degrees, 1050 degrees, 1055 degrees, 1060 degrees, 1065 degrees, 1070 degrees, 1075 degrees, or 1080 degrees about the service loop guide 384. In other embodiments, the energy guides 322A can loop less than approximately 5 degrees or greater than approximately 1080 degrees about the service loop guide 384.

The service loop guide 384 can guide at least one of movement and positioning of the energy guides 322A within the optoelectrical connector 251. The service loop guide 384 can reduce the mechanical strain on the service loop 322L, various cables, guides, and/or other components within the optoelectrical connector 251. As shown in FIG. 3, the service loop 322L includes a portion of the energy guides 322A, in order to reduce the mechanical strain and/or mechanical forces that may impact the energy guides 322A.

The service loop guide 384 can cooperate with the guide bundler 252 so that a user can service the energy guides 322A. For example, the guide bundler 252 can be at least partially removable to expose the energy guides 322A and/or the service loop 322L so that an operator can service, repair, and/or remove the energy guides 322A (or any other component of the optoelectrical connector 251).

The service loop guide 384 and the guide bundler 252 can cooperate to (i) provide a storage area for the energy guides 322A and/or (ii) maintain the organization of the energy guides 322A. The specifics of the service loop guide 384 can vary depending upon the design requirements of the catheter system 100, the optoelectrical connector 251, and/or the specific needs, specifications, and/or desires of the user or operator.

The service loop guide 384 can position components such as the energy guides 322A and/or the service loop 322L. For example, as shown in FIG. 3, the service loop guide 384 can position the service loop 322L portion of the energy guides 322A in a somewhat circular pattern. It is appreciated that the service loop guide 384 can take the form of any suitable geometric structure and that the service loop guide 384 is shown as a circle in FIG. 3 merely for ease of understanding. The service loop guide 384 can define a path that is able to receive a portion of the energy guides 322A so that the portion can form a loop (e.g., the service loop 322L) around the service loop guide 384. The service loop guide 384 can be configured to enable movement of the guide distal end 122D (illustrated in FIG. 1) of each of the energy guides 322A relative to the optoelectrical connector 251.

In certain embodiments, the service loop guide 384 increases the likelihood that a portion of the energy guides 322A (such as the service loop 322L) remains in a looped orientation such that tension or axial movement experienced by the energy guides 322A does not cause the energy guides 322A to kink or otherwise bend at an undesirable angle. This reduces the possibility of damage to the energy guides 322A.

The service loop guide 384 can include a post or other structure having a width, thereby maintaining a spacing or diameter of the portion of the energy guides 322A located within the service loop 322L. The width of the service loop guide 384 may be larger than a minimum bend or kink radius of the energy guides 322A, which may depend on the particular material from which the energy guides 322A are constructed.

In some embodiments, the service loop guide 384 may include a guide receiver (not shown) for receiving a portion of the energy guides 322A, thereby positioning the energy guides 322A towards the handle assembly 128. The guide receiver can be displaced from a portion of the service loop guide 384, about which the energy guides 322A have looped around, thereby providing a spacing between the energy guides 322A within the guide bundler 252.

The service loop guide 384, for example, may include a channel, groove, depression, aperture, or similar passage in the body of the service loop guide 384. Although not shown, the service loop guide 384 may include multiple paths for additional energy guides 322A and/or an electrical cable 386 coupled to the optoelectrical connector 251 to aid in managing and positioning the energy guides 322A and/or the electrical cable 386 through the length of the catheter system 100 to reduce the likelihood of tangling, kinking, or the like. The electrical cable 386 can connect various portions of the handle assembly 128 and/or the optoelectrical connector 251 to any suitable source of power (such as the power source 125, illustrated in FIG. 1).

In other embodiments, the service loop guide 384 can be omitted for the catheter system 100 and the energy guides 322A can form one or more loops (such as the service loop 322L) to provide extra length at the guide distal end 122D only when needed.

As illustrated in the embodiment shown in FIG. 3, the optoelectrical connector 251 also includes the second electrical connector 465 (illustrated in phantom, and illustrated more clearly in FIG. 4) that is configured to interface with the first electrical connector 163 (illustrated in FIG. 1) in the system console 123 so that power and data can be effectively transmitted between the system console 123 and the catheter 102. As noted above, the electrical connection assembly that includes the first electrical connector 163 and/or the second electrical connector 465 can also include the electrical cable 386 that is electrically coupled to the second electrical connector 465 for purposes of more effectively transmitting power and data as desired between the system console 123 and various other components of the catheter system 100 such as the catheter 102.

Figure 4:
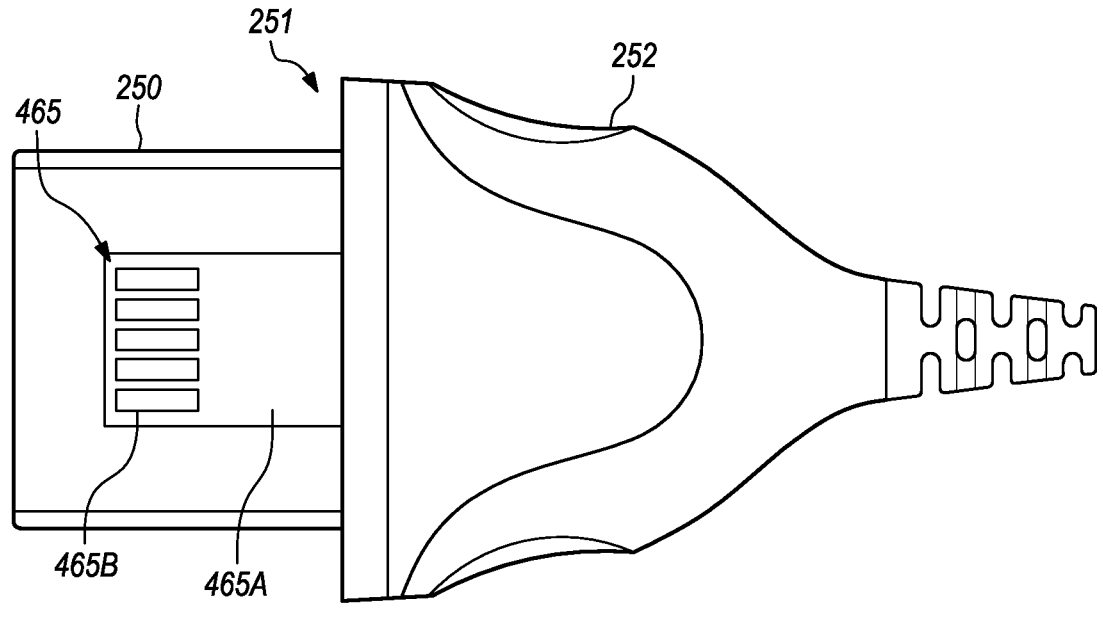
FIG. 4 is a simplified bottom view illustration of the optoelectrical connector assembly illustrated in FIG. 2.

FIG. 4 is a simplified bottom view illustration of the optoelectrical connector 251 illustrated in FIG. 2. More specifically, FIG. 4 is a simplified bottom view illustration of the optoelectrical connector 251 showing the guide coupling housing 250, the guide bundler 252, and the second electrical connector 465 that is positioned within and/or adjacent to the guide coupling housing 250.

As illustrated, the second electrical connector 465 is configured to interface with the first electrical connector 163 (illustrated in FIG. 1) positioned within the system console 123 (illustrated in FIG. 1) to ensure that power and/or data are effectively transmitted between the system console 123 and the catheter 102 (illustrated in FIG. 1) when the optoelectrical connector 251 is mechanically coupled to the system console 123.

The second electrical connector 465 can have any suitable design for purposes of interfacing with the first electrical connector 163. For example, in one non-exclusive embodiment, as shown in FIG. 4, the second electrical connector 465 can include a connector base 465A, such as in the form of a printed circuit board, and a plurality of electrical connection (conduction) pads 465B that are coupled to and/or mounted on the connector base 465A. Each of the plurality of electrical connection pads 465B is configured to interface with a corresponding electrical connection component included as part of the first electrical connector 163. In some embodiments, the electrical connection pads 465B can be recessed within the connector base 465A so as to inhibit unintentional contact, such as by fingers, with the electrical connection pads 465B during use and manipulation of the optoelectrical connector 251. Moreover, the size and/or spacing for the electrical connection pads 465B can also be configured such that a typically sized finger is too large to directly access and contact the electrical connection pads 465B within the recesses. Rather, the fingers would instead generally contact the connector base 465A on either side of the recess. Alternatively, the second electrical connector 465 can have another suitable design, which may also be configured to inhibit unintentional contact with the electrical connection pads 465B. Still alternatively, the second electrical connector 465 can be positioned in another suitable manner that is different than what is specifically shown in FIG. 4.

The second electrical connector 465 can include any suitable number of electrical connection pads 465B to ensure the desired electrical connection between the system console 123 and the catheter 102. For example, in one embodiment, as shown in FIG. 4, the second electrical connector 465 can include five electrical connection pads 465B that are coupled to, mounted on and/or recessed within the connector base 465A. Alternatively, the second electrical connector 465 can include greater than five or less than five electrical connection pads 465B that are coupled to, mounted on and/or recessed within the connector base 465A.

Figure 5:
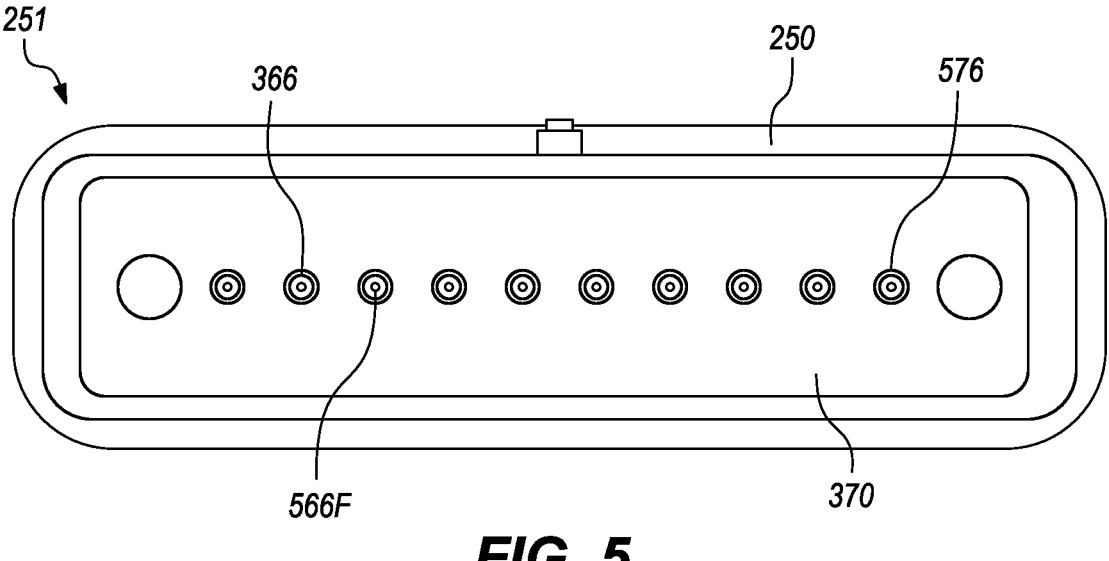
FIG. 5 is a simplified end view illustration of the optoelectrical connector assembly illustrated in FIG. 2.

FIG. 5 is a simplified end view illustration of the optoelectrical connector 251 illustrated in FIG. 2. More particularly, FIG. 5 illustrates a face 566F of each of the ferrules 366 as the ferrules 366 are retained in generally spaced apart desired positions within the ferrule housing 370. In some embodiments, as illustrated, the ferrules 366 are positioned within positioning apertures 576 that are formed into the ferrule housing 370. As shown, the positioning apertures 576 can be sized to have tolerances that enable a loose fit of the ferrules 366 within the positioning apertures 576. Stated in another manner, in certain embodiments, the positioning apertures 576 are slightly larger than a diameter of the ferrules 366 to allow the ferrule 366 to move relative to the ferrule housing 370. With such design, as noted, the ferrules 366 are allowed to float significantly in the ferrule housing 370 to allow for the ferrules 366, and thus the guide proximal end 322P (illustrated in FIG. 3) of the energy guides 322A (illustrated in FIG. 3), to more accurately line up with the energy from the energy source 124 (illustrated in FIG. 1) when the optoelectrical connector 251 is positioned within the console connection aperture 148 (illustrated in FIG. 1) of the system console 123 (illustrated in FIG. 1).

As the optoelectrical connector 251 is advanced into the console connection aperture 148, the ferrules 366 find their place in the console connection aperture 148 due to a chamfered lead-in on the console connection aperture 148. This allows for a tight tolerance on the console connection aperture 148 and the tight tolerances of the outer diameter of the ferrules 366 to drive the fit.

In various embodiments, the ferrule housing 370 can also be selectively adjustable in position within the guide coupling housing 250 to better enable the desired alignment between the energy guides 322A and the energy from the energy source 124. Stated in another manner, in addition to the loose fit between the ferrules 366 and the positioning apertures 576 in the ferrule housing 370, the ferrule housing 370 is also allowed to float (up-and-down and/or side-to-side) inside the assembled guide coupling housing 250. With such design, enabling of the accurate and precise positioning of the guide proximal end 322P of each of the energy guides 322A relative to the energy from the energy source 124 is further enhanced.

Figure 6:
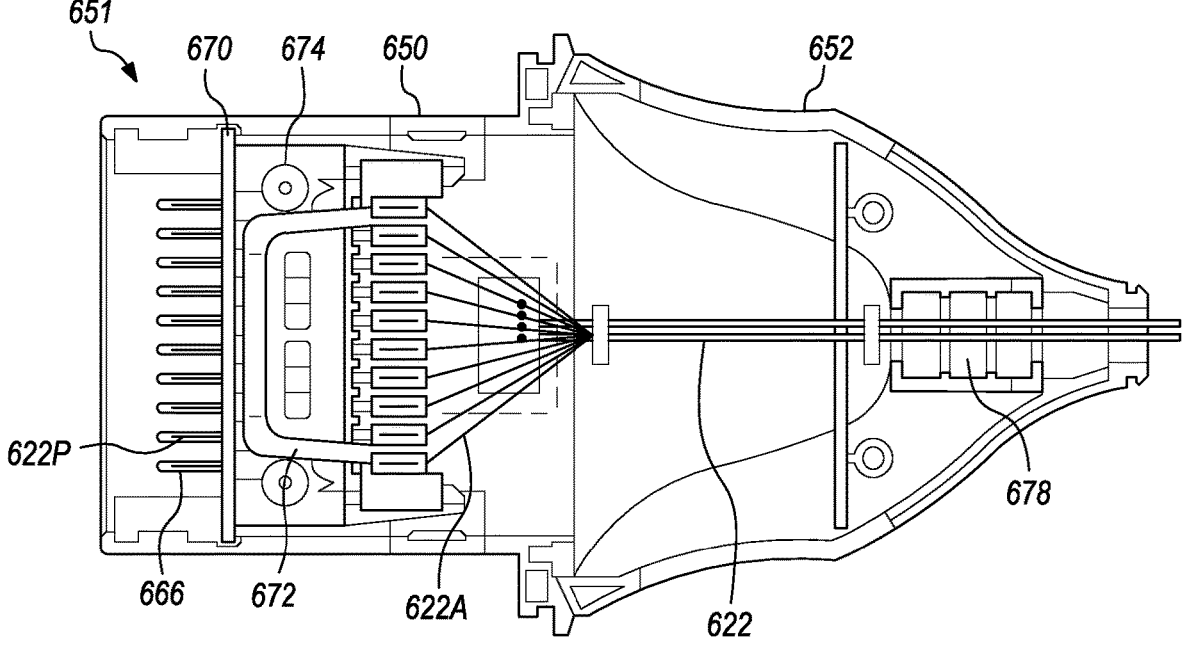
FIG. 6 is a simplified top view illustration of a portion of another embodiment of the optoelectrical connector assembly.

FIG. 6 is a simplified top view illustration of a portion of another embodiment of the optoelectrical connector assembly 651. As shown, the optoelectrical connector 651 is substantially similar to the embodiments of the optoelectrical connector 251 illustrated and described herein above. For example, as illustrated in FIG. 6, the optoelectrical connector 651 again includes the guide coupling housing 650, the guide bundler 652, the ferrules 666, the ferrule housing 670, the resilient plate 672, and the position compensator 674 that are substantially similar in design and function to the corresponding components illustrated and described herein above. Accordingly, such components will not again be described in detail. It is appreciated that the optoelectrical connector 651 can, and likely would, also include the sealing member 260 (illustrated in FIG. 2), the contaminant inhibitor 262 (illustrated in FIG. 2), and the locking mechanism 264 (illustrated in Figure), even though such components are not shown in FIG. 6.

However, in this embodiment, the energy guide bundle 622 and/or the energy guides 622A do not include a service loop 322L as the energy guides 622A are routed through the guide coupling housing 650 and/or the guide bundler 652 of the optoelectrical connector 651. Thus, without the service loop 322L being formed within the optoelectrical connector 651, the routing of the energy guides 622A through the optoelectrical connector 651 is somewhat different than in the previous embodiments. In particular, as shown, the routing of the energy guides 622A as they extend through the guide coupling housing 650 and the guide bundler 652 of the optoelectrical connector 651 includes the guide proximal end 622P of each of the energy guides 622A being positioned within one of the ferrules 666 near the side of the guide coupling housing 650 that faces the console connection aperture 148 (illustrated in FIG. 1) of the system console 123, with the energy guides 622A being positioned at a desired spacing relative to one another. The energy guides 622A then extend through the guide coupling housing 650 to where they are brought closer together, or bundled together, at the guide bundler 652. The energy guide bundle 622, with the energy guides 622A positioned within the shaft jacket 678, then extends with the catheter 102 (illustrated in FIG. 1) toward the balloon 104 (illustrated in FIG. 1).

Figure 7A:
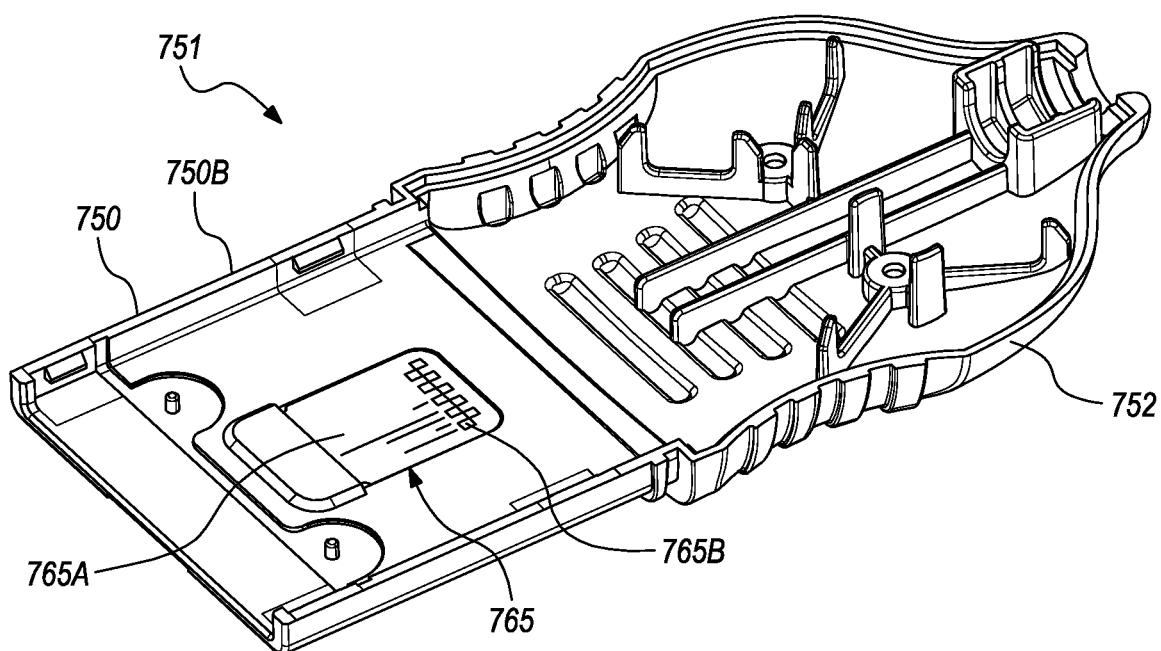
FIG. 7A is a simplified top perspective view illustration of a portion of still another embodiment of the optoelectrical connector assembly.

FIG. 7A is a simplified top perspective view illustration of a portion of still another embodiment of the optoelectrical connector assembly 751. In particular, FIG. 7A is a simplified top perspective view illustration of a portion of the guide coupling housing 750, namely the second housing member 750B, the guide bundler 752, and an embodiment of the second electrical connector 765 that is positioned within and/or adjacent to the guide coupling housing 750. In this embodiment, the design of the second electrical connector 765 is somewhat different than the embodiment illustrated and described herein above.

As illustrated, the second electrical connector 765 is again configured to interface with the first electrical connector 163 (illustrated in FIG. 1) positioned within the system console 123 (illustrated in FIG. 1) to ensure that power and/or data are effectively transmitted between the system console 123 and the catheter 102 (illustrated in FIG. 1) when the optoelectrical connector 751 is mechanically coupled to the system console 123.

As shown in FIG. 7A, the second electrical connector 765 again includes a connector base 765A, such as in the form of a printed circuit board, and a plurality of electrical connection pads 765B that are coupled to and/or mounted on the connector base 765A, and that are configured to interface with corresponding electrical connection components included as part of the first electrical connector 163. It is again appreciated that the second electrical connector 765 can include any suitable number of electrical connection pads 765B, with the number of electrical connection pads 765B again generally coinciding with the number of corresponding electrical connection components included as part of the first electrical connector 163.

Figure 7B:
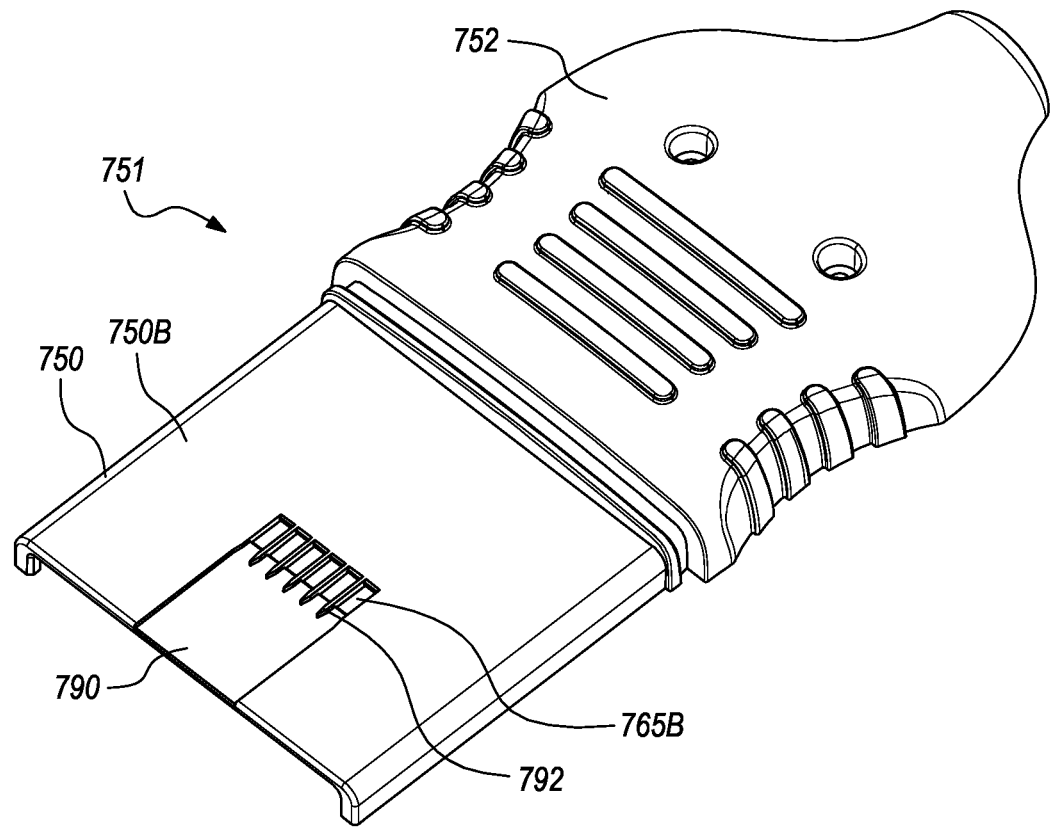
FIG. 7B is a simplified bottom view illustration of the portion of the optoelectrical connector assembly illustrated in FIG. 7A.

FIG. 7B is a simplified bottom view illustration of the portion of the optoelectrical connector assembly 751 illustrated in FIG. 7A. More specifically, FIG. 7B is a simplified bottom perspective view illustration of the portion of the guide coupling housing 750, namely the second housing member 750B, the guide bundler 752, and the second electrical connector 765 that is positioned within and/or adjacent to the guide coupling housing 750, which are illustrated in FIG. 7A.

As shown in FIG. 7B, the second electrical connector 765 is positioned within a recessed area 790 that is formed into the second housing member 750B. As further illustrated, a plurality of spacers 792 are included that extend generally away from the surface of the second housing member 750B within the recessed area 790. The spacers 792 are positioned between the electrical connection pads 765B of the second electrical connector 765. The size and shape of the spacers 792, as well as the spacing between the electrical connection pads 765B of the second electrical connector 765, are specifically designed to inhibit unintentional contact with the electrical connection pads 765B, such as by the fingers of the user or operator of the catheter system 100 (illustrated in FIG. 1), during use and manipulation of the optoelectrical connector 751. Thus, with such design, the electrical connection pads 765B of the second electrical connector 765 are effectively recessed relative to the overall surface of the second housing member 750B in a manner that protects the integrity of the electrical connection pads 765B while still enabling the desired interfacing between the electrical connection pads 765B of the second electrical connector 765 and the corresponding electrical connection components included as part of the first electrical connector 163.

The present technology is also directed toward methods for treating a treatment site within or adjacent to a vessel wall, with such methods utilizing the devices disclosed herein.

In summary, based on the various embodiments of the present invention illustrated and described in detail herein, the catheter systems and related methods can include a catheter configured to advance to a vascular lesion, such as a calcified vascular lesion or a fibrous vascular lesion, at a treatment site located within or adjacent a blood vessel within a body of a patient. The catheter includes a catheter shaft, and an inflatable balloon that is coupled and/or secured to the catheter shaft. The balloon can include a balloon wall that defines a balloon interior. The balloon can be configured to receive a catheter fluid within the balloon interior to expand from a deflated state suitable for advancing the catheter through a patient's vasculature, to an inflated state suitable for anchoring the catheter in position relative to the treatment site.

In certain embodiments, the catheter systems and related methods utilize an energy source, e.g., a light source such as a laser source or another suitable energy source, which provides energy that is guided by one or more energy guides, e.g., light guides such as optical fibers, which are disposed along the catheter shaft and within the balloon interior of the balloon to create a localized plasma in the catheter fluid that is retained within the balloon interior of the balloon. The energy guide can be used in conjunction with a plasma generator that is positioned at or near a guide distal end of the energy guide within the balloon interior of the balloon located at the treatment site. The creation of the localized plasma can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles (also sometimes referred to simply as "plasma bubbles") can generate one or more pressure waves in the catheter fluid retained within the balloon interior of the balloon and thereby impart pressure waves onto and induce fractures in the vascular lesions at the treatment site within or adjacent to the blood vessel wall within the body of the patient. In some embodiments, the energy source can be configured to provide sub-millisecond pulses of energy, e.g., light energy, to initiate the plasma formation in the catheter fluid within the balloon to cause the rapid bubble formation and to impart the pressure waves upon the balloon wall at the treatment site. Thus, the pressure waves can transfer mechanical energy through an incompressible catheter fluid to the treatment site to impart a fracture force on the intravascular lesion. Without wishing to be bound by any particular theory, it is believed that the rapid change in catheter fluid momentum upon the balloon wall that is in contact with the intravascular lesion is transferred to the intravascular lesion to induce fractures to the lesion.

Importantly, the catheter systems and related methods disclosed herein further include an optoelectrical connector that is configured to ensure proper alignment and coupling of ferrules that each retain a portion of one of the one or more energy guides to a system console that can include various operational components of the catheter system such as the energy source, a power source, and at least a portion of a system controller. More particularly, through use of the optoelectrical connector having features of the present invention, the one or more energy guides can be properly aligned within a console connection aperture of the system console so that energy from the energy source is more precisely and accurately directed into a proximal end of each of the one or more energy guides before such energy is guided by the one or more energy guides into the balloon interior. In various embodiments, the optoelectrical connector can be further configured to ensure that a guide face at the proximal end of the energy guides into which the energy from the energy source is directed is substantially free from dust and particulates, which may otherwise contaminate the guide face.

In many embodiments, the optoelectrical connector is further configured to ensure appropriate electrical connection is established between the system console and the catheter such that power and data can be effectively transmitted between the system console and the catheter. More particularly, an electrical connector integrated as part of the optoelectrical connector is configured to interface with a corresponding electrical connector within the system console to ensure that power and data can be effectively transmitted between the system console and the catheter.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A catheter system for treating a treatment site within or adjacent to a blood vessel within a body of a patient, the catheter system comprising:

a catheter;

a system console including a console connection aperture;

an energy source that is configured to generate energy;

one or more energy guides that are configured to receive the energy from the energy source; and an optoelectrical connector that is coupled to the catheter, the optoelectrical connector including (i) a guide coupling housing that retains at least a portion of each of the one or more energy guides, the guide coupling housing being configured to be selectively mechanically connected to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source; and (ii) at least a portion of an electrical connector assembly that extends along an exterior surface of the guide coupling housing and that transmits at least one of power and data between the system console and the catheter when the guide coupling housing is retained within the console connection aperture.

2. The catheter system of claim 1 wherein the electrical connection assembly includes a first electrical connector that is positioned within the system console, and a second electrical connector that is positioned adjacent to the guide coupling housing, the second electrical connector being configured to interface with the first electrical connector when the guide coupling housing is retained within the console connection aperture.

3. The catheter system of claim 2 wherein the second electrical connector includes a connector base and a plurality of electrical connection pads that are electrically coupled to the connector base.

4. The catheter system of claim 2 wherein the electrical connection assembly further includes an electrical cable that is electrically connected to the second electrical connector and the catheter.

5. The catheter system of claim 1 wherein the energy source is positioned within the system console.

6. The catheter system of claim 1 wherein the optoelectrical connector further includes (i) a plurality of ferrules, each of the plurality of ferrules being configured to retain a portion of one of the one or more energy guides, and (ii) a ferrule housing having a plurality of positioning apertures that are each configured to retain at least a portion of one of the plurality of ferrules spaced apart from one another, each of the plurality of positioning apertures being larger than a diameter of the ferrule that is retained therein to allow the ferrule to move relative to the positioning aperture.

7. The catheter system of claim 6 wherein the ferrule housing is adjustably positioned within the guide coupling housing so that the ferrule housing is movable relative to the guide coupling housing.

8. The catheter system of claim 6 wherein the guide coupling housing includes a console facing side; and wherein the plurality of ferrules are recessed from the console facing side of the guide coupling housing.

9. The catheter system of claim 1 wherein the optoelectrical connector further includes a sealing member that seals the connection between the guide coupling housing and the console connection aperture.

10. The catheter system of claim 1 wherein the optoelectrical connector further includes a contaminant inhibitor that is positionable about at least a portion of the guide coupling housing, the contaminant inhibitor being configured to inhibit dust and particulates from contaminating a face of each of the one or more energy guides.

11. The catheter system of claim 1 wherein the optoelectrical connector further includes a locking mechanism that is configured to selectively lock the guide coupling housing in position when the guide coupling housing is being retained within the console connection aperture.

12. The catheter system of claim 1 wherein the system console further includes an optical sensor and an actuator; the optical sensor is configured to sense a position of the guide coupling housing relative to the console connection aperture, and the optical sensor is further configured to initiate the actuator that mechanically draws the guide coupling housing into place within the console connection aperture.

13. The catheter system of claim 1 further comprising a balloon that is configured to be positioned substantially adjacent to the treatment site, the balloon including a balloon wall that defines a balloon interior, the balloon being configured to retain a catheter fluid within the balloon interior, each of the one or more energy guides including a guide distal end that is configured to be positioned within the balloon interior, each of the one or more energy guides being configured to guide the energy from the energy source through the energy guide and into the balloon interior, and each of the one or more energy guides guiding the energy from the energy source into the balloon interior generates plasma in the catheter fluid within the balloon interior.

14. The catheter system of claim 1 wherein at least one of the one or more energy guides includes an optical fiber, and the energy source including a laser.

15. A method for treating a treatment site within or adjacent to a blood vessel within a body of a patient, the method comprising the steps of:

provide a system console including a console connection aperture;

generating energy with an energy source;

receiving the energy from the energy source with one or more energy guides;

coupling an optoelectrical connector to a catheter, the optoelectrical connector including a guide coupling housing and at least a portion of an electrical connector assembly that extends along an exterior surface of the guide coupling housing;

retaining at least a portion of each of the one or more energy guides with the guide coupling housing of the optoelectrical connector;

selectively mechanically connecting the guide coupling housing to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source; and transmitting at least one of power and data between the system console and the catheter with the electrical connector assembly when the guide coupling housing is retained within the console connection aperture.

16. The method of claim 15 wherein the step of transmitting includes positioning a first electrical connector within the system console and positioning a second electrical connector adjacent to the guide coupling housing, the second electrical connector including a connector base and a plurality of electrical connection pads that are coupled to the connector base, the second electrical connector being configured to interface with the first electrical connector when the guide coupling housing is retained within the console connection aperture.

17. The method of claim 16 wherein the step of positioning the second electrical connector includes the second electrical connector including a connector base and a plurality of electrical connection pads that are coupled to the connector base.

18. The method of claim 15 wherein the step of coupling the optoelectrical connector includes the optoelectrical connector further including a plurality of ferrules, and a ferrule housing having a plurality of positioning apertures; and further comprising the steps of retaining a portion of one of the one or more energy guides with each of the plurality of ferrules, and retaining at least a portion of one of the plurality of ferrules spaced apart from one another with each of the plurality of positioning apertures; wherein each of the plurality of positioning apertures is larger than a diameter of the ferrule that is retained therein to allow the ferrule to move relative to the positioning aperture; and wherein the ferrule housing is adjustably positioned within the guide coupling housing so that the ferrule housing is movable relative to the guide coupling housing.

19. The method of claim 15 wherein the step of providing the system console includes the system console further including an optical sensor and an actuator; and further comprising the steps of sensing a position of the guide coupling housing relative to the console connection aperture with the optical sensor, and initiating the actuator that mechanically draws the guide coupling housing into place within the console connection aperture based on the sensed position of the guide coupling housing relative to the console connection aperture.

20. A catheter system for treating a treatment site within or adjacent to a blood vessel within a body of a patient, the catheter system comprising:

a catheter;

a system console including a console connection aperture, an optical sensor and an actuator;

an energy source that is configured to generate energy;

one or more energy guides that are configured to receive the energy from the energy source; and an optoelectrical connector that is coupled to the catheter, the optoelectrical connector including:

(i) a guide coupling housing that retains at least a portion of each of the one or more energy guides, the guide coupling housing being configured to be selectively mechanically connected to the system console with at least a portion of the guide coupling housing being configured to fit and be selectively retained within the console connection aperture so that the one or more energy guides are adjustably aligned within the guide coupling housing and relative to the energy from the energy source to receive the energy from the energy source, the optical sensor being configured to sense a position of the guide coupling housing relative to the console connection aperture, and being further configured to initiate the actuator that mechanically draws the guide coupling housing into place within the console connection aperture;

(ii) at least a portion of an electrical connector assembly that is positioned adjacent to the guide coupling housing and that transmits at least one of power and data between the system console and the catheter when the guide coupling housing is retained within the console connection aperture, the electrical connection assembly including a first electrical connector that is positioned within the system console, and a second electrical connector that is positioned adjacent to the guide coupling housing, the second electrical connector being configured to interface with the first electrical connector when the guide coupling housing is retained within the console connection aperture, the second electrical connector including a connector base and a plurality of electrical connection pads that are coupled to the connector base;

(iii) a plurality of ferrules, each of the plurality of ferrules being configured to retain a portion of one of the one or more energy guides; and (iv) a ferrule housing having a plurality of positioning apertures that are each configured to retain at least a portion of one of the plurality of ferrules spaced apart from one another, each of the plurality of positioning apertures being larger than a diameter of the ferrule that is retained therein to allow the ferrule to move relative to the positioning aperture, the ferrule housing being adjustably positioned within the guide coupling housing so that the ferrule housing is movable relative to the guide coupling housing.

* * * * *